United States Patent [19]
Sari et al.

[11] Patent Number: 5,663,196
[45] Date of Patent: Sep. 2, 1997

[54] METHODS FOR TREATING NEOPLASTIC DISORDERS

[75] Inventors: Nil Sari, Istanbul, Turkey; Hanzade Dogan, North Quincy; John K. Snyder, Boston, both of Mass.

[73] Assignee: Boston University, Boston, Mass.

[21] Appl. No.: 116,689

[22] Filed: Sep. 3, 1993

[51] Int. Cl.$^6$ .................................................. A61K 31/34
[52] U.S. Cl. ......................................................... 514/468
[58] Field of Search ............................................. 514/468

[56] References Cited

PUBLICATIONS

Seto, M., et al., *Chem. Pharm. Bull.*, 1989, 36, 2423.
Lee, K.–H., et al., *Science*, 1977, 196, 533.

*Primary Examiner*—Jerome D. Goldberg
*Attorney, Agent, or Firm*—Baker & Botts, LLP

[57] ABSTRACT

A method for treating neoplastic disorders such as lymphomas, adenocarcinomas, mastocytomas, myelomas, pulmonary tumors, and macrophage tumors is provided. The method utilizes compounds containing a cross-conjugated cyclopentenone structure, but lacking an $\alpha,\beta$ unsaturated $\gamma$-lactone moiety.

6 Claims, 10 Drawing Sheets

METHODS FOR TREATING NEOPLASTIC DISORDERS

BACKGROUND OF THE INVENTION

1. Field of the Invention

The present invention is directed to methods of treating neoplastic diseases. More particularly, methods for using compounds which have a cross-conjugated cyclopentenone moiety, and which lack an $\alpha,\beta$-unsaturated $\gamma$-lactone moiety are provided.

2. Description of the Prior Art

Cellular homeostasis is a delicate balance between cell production and cell removal. Homeostasis depends to a large extent on two alternative modes of existence of animal cells: the quiescent and the proliferative. The growth and division of normal cells is usually regulated by the action of various endogenous stimulators and inhibitors. When this delicate balance is perturbed, hyperproliferation or neoplasia may develop.

Neoplastic disorders constitute a major health problem in the world today. Few antineoplastic agents have the dual beneficial properties of both efficacy and reduced toxicity. The vast majority of antineoplastic agents currently in use are generally both relatively non-tumor specific, as well as toxic to the individual being treated. For example, typical toxicities associated with antitumor therapeutic agents include immune suppression, bone marrow depression, alopecia, and a host of other unwanted side effects. The key in identifying beneficial antineoplastic agents is in isolating agents which are capable of inhibiting neoplastic growth without adversely affecting normal cell growth.

An excellent source of agents having the potential for treating neoplastic conditions is plants such as herbs. There is substantial history of the use of herbal medicines for treating a variety of diseases. Although certain claims of these herbal medicaments can be discounted, others necessitate closer scrutiny. Isolation and identification of compounds from plants and herbs provides clues to beneficial pharmaceutical agents.

Turkish herbal medicines are somewhat unique in this regard. Since Istanbul was an intersection of major trade routes in older civilizations, Turkish traditional medicines readily incorporated the knowledge and herbal applications of the highly advanced Chinese, Aryuvedic (Indian), Persian and other Islamic medicines into their own system. In the Ottoman Empire, the traditional medical system reached a highly developed state, well beyond that initiated by foreign influence, due to the presence of a large number of plant species endemic to the area now known as Turkey.

One such "medicine" which had been used through the centuries to treat "conditions" of internal blockages was called "hindiba" in Turkish. Three different primary herbal species, *Cichorium endivia* (cultivated endive), *Lactuca scariola* (cultivated scariola or Italian endive), and wild chicory (*C. intybus*) were all used to prepare hindiba, along with numerous other local substitute species (such as Taraxacum species and others). The ancient Turkish, Islamic and other medicinal texts suggest that hindiba prepared from wild chicory was the most important historical agent in treating internal blockages. The Ottoman texts also cautioned that hindiba was somewhat unstable to aging and to heat.

For years investigators used cytotoxicity against tumor cells as a criterion for assessing antitumor activity. Compounds which were not cytotoxic in those assays were not considered useful in tumor suppression or control.

The prior art reveals that compounds (some of which are of herbal origin) having a $O{=}C{-}C{=}CH_2$ moiety as part of an ester, ketone, or lactone, and more particularly as an $\alpha,\beta$-unsaturated $\gamma$-lactone moiety, may have such "antineoplastic" or "antitumor" properties. However, these properties are related to the cytotoxic properties of the compounds, and not selective antineoplastic properties. Most of these compounds were tested using the classic cell lines L1210 or P388 lymphoma cells, which readily respond to cytotoxic agents. A number of these compounds are sesquiterpene lactones having an $\alpha,\beta$-unsaturated $\gamma$-lactone group. It is generally recognized that these compounds of the prior art, which were identified as having "anticancer" properties, were exhibiting nonselective cytotoxic properties associated with the $\alpha,\beta$-unsaturated $\gamma$-lactone moieties. The compounds were toxic to all cells and had little or no therapeutic window. The cytotoxic properties associated with compounds containing an $\alpha,\beta$-unsaturated $\gamma$-lactone moiety limit their therapeutic effectiveness since they affect normal cells as well as neoplastic cells.

Since *Cichorium intybus* and *C. endivia* were known medicinally, these species were also scrutinized for biologically significant natural products, with particular interest paid to the sesquiterpene lactones bearing the $\alpha,\beta$-unsaturated $\gamma$-lactone moiety, since the prior art was such as to equate cytotoxic with antineoplastic activity. Indeed, the well-known sesquiterpene lactones such as lactucin, lactupicrin, 8-deoxylactucin, and 15-O-$\beta$-D-glucopyranosyl-8-deoxylactucin, all of which bear the $\alpha,\beta$-unsaturated $\gamma$-lactone moiety, were found in these Cichorium species and were examined for cytotoxic activity. See Schenck, G., Graf, H. *Arch. Pharm.* (*Weinheim*) 1936, 274, 537; Leclercq, E. *J. Chromatogr.* 1984, 283, 441; Pyrek, J. St. *Phytochemistry* 1985, 24, 186; Seto, M., Miyase, T., Umehara, K., Ueno, A., Hirano, Y., Otani, N. *Chem. Pharm. Bull.* 1989, 36, 2423. 11$\beta$,13-Dihydrolactucin and its 15-O-$\beta$-D-glucopyranoside were also found in *C. intybus*, but since these compounds did not bear the $\alpha,\beta$-unsaturated $\gamma$-lactone moiety, they either were not tested for cytotoxic activity, or were tested but were found to be non-cytotoxic since no activity was reported.

Lee and coworkers suggested in 1977 that the cyclopentenone unit, commonly found in pseudoguaianolides such as helenalin, plenolin, and tenulin, is responsible for in vitro cytotoxic activity against cancer cell lines; Lee, K.-H., Hall, I. H., Mar, E.-C., Starnes, C. O., ElGebaly, S. A., Waddell, T. G., Hadgraft, R. I., Ruffner, C. G., Weidner, I. *Science* 1977, 196, 533. These workers, however, were still equating nonselective cytotoxicity with antitumor activity, and more importantly, the compounds they considered did not possess the cross-conjugated cyclopentenone structure which is crucial for the activity we have observed. In summary, the prior art led away from the compounds of this invention by focusing on cytotoxicity. Compounds which did not exhibit cytotoxicity were not deemed to be of interest as antineoplastic agents.

SUMMARY OF THE INVENTION

In accordance with the present invention, a method for treating neoplastic disorders is provided. The method employs the use of agents isolated from herbs. Specifically, the active agents of the present invention have a cross-conjugated cyclopentenone structure. The active agents of the present invention lack an $\alpha,\beta$-unsaturated $\gamma$-lactone moiety, which limited the therapeutic effectiveness of prior art compounds.

One embodiment of the present invention is to provide a method for treating neoplasia using agents having a cross-conjugated cyclopentenone structure, and more specifically, using the specific active agents disclosed and claimed herein. The neoplastic disorders responsive to the active agents disclosed and claimed herein include, but are not limited to, lymphomas, adenocarcinomas, mastocytomas, myelomas, pulmonary cancers, and neoplastic disorders involving macrophages.

An additional embodiment of the present invention is to provide compositions of active agents having a cross-conjugated cyclopentenone structure, but lacking the $\alpha,\beta$-unsaturated $\gamma$-lactone moiety.

It has been discovered that the active agents described and claimed herein have antineoplastic effects. These and other advantages of the present invention will become apparent from the following detailed description.

DETAILED DESCRIPTION OF THE INVENTION

Figure 1A:
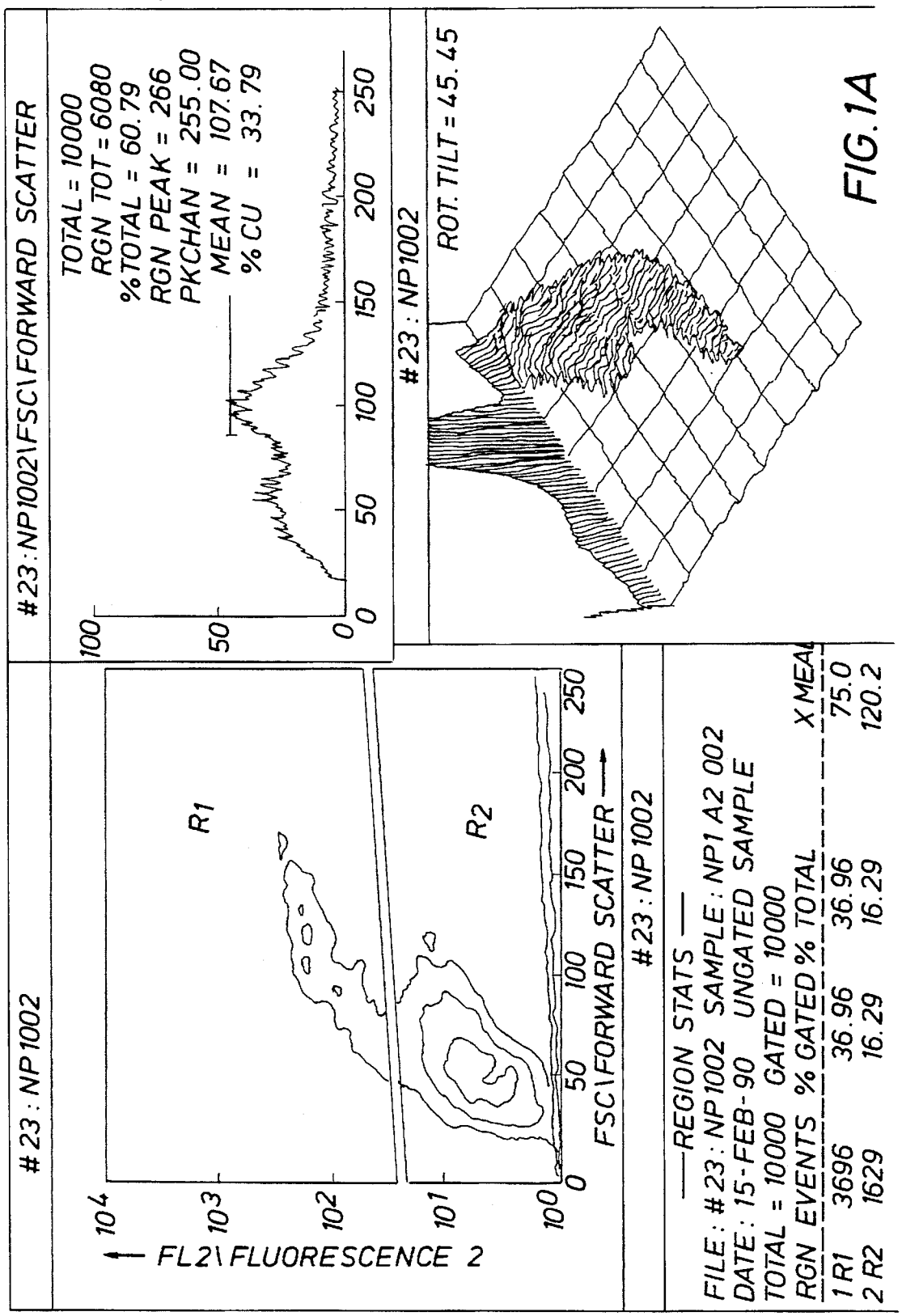
FIG. 1 is the fluorescence activated cell sorter (FACS) scans of LS cells treated with the active agent of the present invention.

In accordance with the present invention, compounds having antineoplastic (anticancer) effects are provided. Also provided is a method for treating neoplastic diseases using effective amounts of the active agents of the present invention. The term "neoplastic" as used herein refers to progressive and indefinite multiplication of cells under conditions that would not elicit, or would cause cessation of multiplication of normal cells. The term "hyperproliferative" refers to an abnormal multiplication or increase in the number of normal cells in a normal arrangement.

The active agents of the present invention have a cross-conjugated cyclopentenone structure as the pharmacophore:

wherein each or any of $R_1$, $R_2$, $R_3$, $R_4$, $R_5$, and $R_6$ is (1) a substituent selected from group consisting of hydrogen (H—), halogen (for example, chloro, fluoro, or bromo), hydroxyl (—OH), alkoxyl (—OR'), acyl (—C(O)—R'), carboxyl (—C(O)—OH), carboxyl esters (—C(O)—OR'), amido (—C(O)—NR'$_2$), amino (—NR'$_2$), nitro (—NO$_2$), nitroso (—NO), azo (—N=N—), diazonium (—N$_2$$^\oplus$), azido (—N$_3$), hydrazino (—NR'—NR'$_2$), cyano (NC—), isocyano (CN—), cyanato (NCO—), isocyanato (OCN—), thioether (—SR'), thiol (—SH), sulfoxide (—S(O)—R'), sulfone (—S(O)$_2$R'), sulfonic acid (HO$_3$S—), sulfonyl esters (R'O$_3$S—), sulfinic acid (HO$_2$S—), sulfinyl esters (R'O$_2$S—), sulfenic acid (HOS—), sulfenyl esters (R'OS—), phospho (—OP(OR$^1$)$_2$), phosphono ((R'O)$_2$P—), or phosphine (—PR'$_2$), where R' is an alkyl, alkenyl, or alkynyl group of 1–5 carbons; (2) an unsaturated or saturated aliphatic, alicyclic or aromatic hydrocarbon radical having from 1–50 carbon atoms, preferably 1–25 carbon atoms, and most preferably 1–15 carbon atoms, which can be substituted with one or more of the substituents of (1) above; (3) a heterocyclic group having about 1–13 carbon atoms; (4) a glycoside residue; or (5) a peptide residue. Two or more of $R_2$, $R_3$, $R_4$, $R_5$ and $R_6$ groups may be combined to form any of the above listed cyclic moieties. The substituents may be arranged in cyclic or acyclic form, as long as the cross-conjugated cyclopentenone pharmacophore retains activity. Activity is a significant response in an in vitro or in vivo bioassay such as described herein. "X" may be oxygen (O), sulfur (S), nitrogen as imines (NR') or hydrazones (NR'—NR'$_2$), where R' is an alkyl, alkenyl or alkynyl group of 1–5 carbons. It is critical that the active agent not have an $\alpha,\beta$ unsaturated $\gamma$-lactone moiety.

In a preferred embodiment, the active agent has the structure:

where X is either O or S, and wherein each or any of $R_1$ and $R_2$ is a substituent selected from group consisting of methyl, ethyl, propyl or butyl; and wherein each or any of $R_3$, $R_4$ and $R_6$ is a substituent selected from the group consisting of hydrogen, methyl, ethyl, propyl, or butyl; wherein $R_5$ is selected from the group consisting of hydroxymethyl or hydroxyethyl; and where the agent does not have an $\alpha,\beta$ unsaturated $\gamma$-lactone moiety.

Active agents of the present invention have the cross-conjugated cyclopentenone pharmacophore and are preferably compounds having the structure:

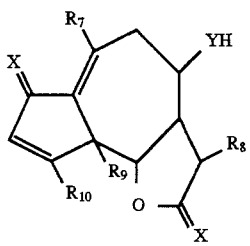

wherein each or any of $R_7$, $R_8$, $R_9$, and $R_{10}$ is (1) a substituent selected from group consisting of hydrogen (H—), halogen (for example, chloro, fluoro, or bromo), hydroxyl (—OH), alkoxyl (—OR'),

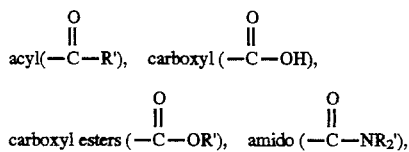

amino (—NR'$_2$), nitro (—NO$_2$), nitroso (—NO), azo (—N=N—), diazonium (—N$_2^{\oplus}$), azido (—N$_3$), hydrazino (—NR'—NR'$_2$), cyano (NC—), isocyano (CN—), cyanato (NCO—), isocyanato (OCN—), thioether (—SR'), thiol (—SH),

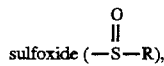

sulfone (—S(O)$_2$R'), sulfonic acid (HO$_3$S—), sulfonyl esters (R'O$_3$S—), sulfinic acid (HO$_2$S—), sulfinyl esters (R'O$_2$S—), sulfenic acid (HOS—), sulfenyl ester (R'OS—),

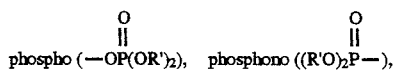

or phosphine (—PR'$_2$), where R' is an alkyl, alkenyl or alkynyl of 1–5 carbons; or (2) an unsaturated or saturated aliphatic, alicyclic or aromatic hydrocarbon radical having from 1–5 carbon atoms which can be substituted with one or more of the substituents of (1) above. "X" may be oxygen (O), sulfur (S), nitrogen as imines (=NR') or hydrazones (NR'NR'$_2$). "Y" may be oxygen (O), sulfur (S), or nitrogen as imino (NR'), or hydrazones (—NR'NR'$_2$). R' is an alkyl, alkenyl or alkynyl group of 1–5 carbons.

Representative active agents or compounds useful in the present invention include, but are not limited to sesquiterpene lactones having a cross-conjugated cyclopentenone structure. Useful sesquiterpene lactones include, but are not limited to, the guaianolide or the pseudoguaianolide sesquiterpene lactones having a cross-conjugated cyclopentenone.

Active agents of the present invention also include, but are not limited to, the following natural products, all of which are also guaianolide sesquiterpene lactones, and contain the pharmacophore but not the α,β-unsaturated γ-lactone moiety: achillin, anhydroaustricin, anhydrogrossmizin, austricin, badkhysin, dehydroaustricin, dehydrogrossmizin, desacetylmatricarin, ferulidin, ferulin, grossmizin, isobadkhysin, jacquinelin, matricarin, 8-hydroxyachillin, and 15-O-β-D-glucopyranosyl-8-deoxylactucin.

Most preferable is a guaianolide sesquiterpene lactone derived from lactucin. Even more preferable is 11β,13-dihydrolactucin, the structure of which is:

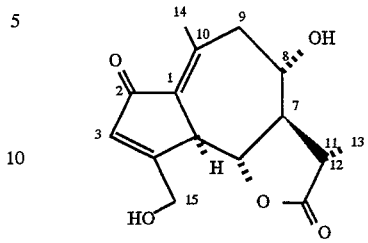

Active agents useful in the present invention lack the α,β unsaturated γ-lactone moiety which rendered the prior art compounds cytotoxic and limited their therapeutic effectiveness. The phrase "active agent" as used herein refers to compounds having a cross-conjugated cyclopentenone, but lacking an α,β unsaturated γ-lactone moiety. The phrase preferred "purified active agent" refers to 11β,13-dihydrolactucin. The IUPAC name for the preferred purified active agent is: 3,6-dimethyl-4-hydroxy-9-hydroxymethyl-3,3a,4,5,9a,9b-hexahydroazuleno[4,5-b]furan-2,7-dione.

The active agents described herein may be isolated from plants or herbs, or may be produced synthetically. *C. intybus* (wild chicory) is most useful for isolation and preparation of said agents, but other plant species such as *Cichorium endivia* (cultivated endive) and *L. scariola* (cultivated scariola or Italian endive) from which compounds having the active pharmacophore may be isolated and purified are also acceptable. Other species such as Taraxacum species may also be used to isolate the active agents of the present invention. Alternatively, the active agents may be produced by chemical modification of compounds isolated from other sources, or may be produced synthetically.

The following species listed in Table 1 are considered likely to also produce guaianolide sesquiterpene lactones which bear the pharmacophore, either with or without the α,β-unsaturated γ-lactone moiety. Those species marked with an asterisk (*) are already known to produce such compounds. It is also likely that other representatives of the genera listed here will also produce compounds bearing the pharmacophore, even though the species itself is not included in this list.

TABLE 1

| Species Likely to Produce Active Agents | | |
|---|---|---|
| Artemisia species: | A. leucodes* | A. bigelovii | A. tilesii* |
| | A. leukodia* | A. frigida* | A. douglasiana* |
| | A. lanata* | A. caucasica* | |
| Achillea species: | A. lanulosa* | A. millefolium | |
| Ambrosia species: | A. trifida | A. artemisifolia | |
| Angelica species: | A. pubens* | | |
| Helenium species: | H. virginium | H. autumnale | |
| Ferula species: | F. oopoda* | | |
| Hypochoeris species: | H. radicata* | | |
| Lactuca species: | L. virosa* | L. serriola* | L. scariola |
| Launaea species: | L. mucronata* | | |
| Leontodon species: | L. autumnale* | | |
| Matricaria species: | M. chamomilla* | M. matricarioides | |
| Sonchus species: | S. oleraceus | S. jacquini* | S. pinnatus* |
| | S. radicata* | | |

The active agents may be extracted from herbal species using steam distillation and/or by using a purification scheme such as, but not limited to, the scheme outlined below in Scheme 1 (Example 2). Other means for extracting the active agents may be used. It will be appreciated that active agents having the pharmacophore structure may have different solubilities than 11β,13-dihydrolactucin, and purification schemes will necessarily be modified accordingly. However, by using the described bioassay-guided purification scheme, one skilled in the art can isolate other suitable active agents.

The active agents may be susceptible to degradation by heat, so techniques which promote the extraction of the active agents from herbs should be conducted under minimal heating conditions. Such techniques include, but are not limited to steam distillation at temperatures of about 35° C. to about 60° C., under reduced pressure, and preferably about 40° C. to about 50° C. Reduced pressure of about 5 to about 35 Torr, and preferably about 10 to about 25 Torr promotes extraction of the active agents. The crude aqueous extract may be filtered to remove residual materials.

Isolation of the active agents of the present invention from crude aqueous and/or alcoholic extracts and distillates may be accomplished by partitioning of the aqueous medicinal preparation between different solvents to separate the components on the basis of solubility. Any technique for isolating compounds having the active pharmacophore may be used to isolate the active agents from herbs or other sources. Those skilled in the art will appreciate that various isolation schemes can be used. Various techniques which rely on selective partitioning, chromatography, specific binding, or other techniques can be used. A preferred approach is silica gel flash chromatography and reverse phase $C_{18}$ chromatography. After each step in the isolation procedure, a small sample may be analyzed using in vitro bioassays or other suitable techniques in order to determine which fraction contains the active agent. The in vitro bioassays employed are preferably those which are recognized as useful in predicting antineoplastic and viability response and are useful in testing for in vivo activity. The in vitro bioassays useful for identifying active agents include, but are not limited to, $^3$H-thymidine incorporation, trypan blue dye exclusion, DNA fragmentation, chromium release, and protein synthesis inhibition assays. Other bioassays may also be used. A bioassay-guided isolation method led to identification of the active agents disclosed and claimed herein (compounds having a cross-conjugated cyclopentenone structure) and, specifically to 11β,13-dihydrolactucin as the preferred purified active agent.

The active agent may be characterized by techniques known to those skilled in the art which are useful for identifying complex chemical structures. Such techniques include, but are not limited to, spectroscopic methods such as $^1$H and/or $^{13}$C nuclear magnetic resonance (NMR) spectroscopy, infrared (IR), and/or ultraviolet (UV) spectroscopy. Preferable is NMR spectroscopy using deuterated solvents such as, but not limited to, $CD_3OD$. Also useful in identification is mass spectroscopic (MS) analysis, preferably high resolution mass spectroscopic (HRMS) analysis. Also useful is homonuclear and heteronuclear correlated spectroscopy (COSY). Selective Insensitive Nuclei Enhanced by Polarization Transfer (INEPT) studies may be used to reveal finer structural details. Other techniques may be employed depending on what may be generally known about the compound, for example, its source, selective solubilities, chromatographic behavior, etc.

The active agents of the present invention may be administered orally, intravenously, intranasally, rectally, or by any means which delivers an effective amount of the active agent to the tissue or site to be treated. Suitable dosages are those which achieve the desired endpoint. It will be appreciated that different dosages may be required for treating different neoplastic disorders. An effective amount of an active agent is that amount which causes a significant decrease in neoplastic cell count, growth, or size. Neoplastic disorders responsive to the active agents of the present invention include, but are not limited to, lymphomas, adenocarcinomas, mastocytomas, myelomas, pulmonary tumors, sarcomas and macrophage tumors.

Those having ordinary skill in the art will be able to ascertain the most effective dose and times for administering the active agents of the present invention, considering route of delivery, metabolism of the compound, and other pharmacokinetic parameters such as volume of distribution, clearance, age of the subject, etc.

The active agents may be administered along with a pharmaceutical carrier and/or diluent. The active agents of the present invention may be administered as the various fraction isolated (as, for example, the fractions noted in Scheme 1), or as the preferred purified active agent, or as combinations of these. The active agents of the present invention may also be administered in combination with other agents, for example, in association with other chemotherapeutic or immunostimulating drugs or therapeutic agents.

The present invention is exemplified in terms of in vitro and in vivo activity against various neoplastic and normal cell lines. The test cell lines employed in the in vitro assays are well recognized and accepted as models for antitumor activity in animals. The term "animals" as used herein includes, but is not limited to, mice, rats, domesticated animals such as, but not limited to cats and dogs, and other animals such as, but not limited to cattle, sheep, pigs, horses, and primates such as, but not limited to monkeys and humans. The mouse experimental tumor in vivo assays are also well recognized and accepted as predictive of in vivo activity in other animals such as, but not limited to, humans. Human treatment efficacy has also been established through the clinical observation and monitoring of a human subject treated with the active agents described herein. It is well recognized and established in the art that a clinical case report is a valuable and important indicator of clinical effectiveness and utility.

The following examples serve to illustrate specific embodiments of the invention, but should not be considered as a limitation on the scope of the invention.

EXAMPLES

Example 1

Extraction of *C. intybus*.

In this Example, it is shown how one may obtain an initial extract containing active agents from herbs. Leaves of *C. intybus* were collected in the vicinity of Istanbul, Turkey in the spring before flowering and also in the late fall immediately after rainfall. The freshly collected leaves (200 g) were cut into small pieces and homogenized by pounding in a ceramic mortar, then placed in a round-bottomed flask (1000 mL capacity) with distilled water (400 mL). The flask was placed on a rotary evaporator with the flask immersed in a warm water bath maintained at 40°–50° C. Reduced pressure of 10–25 Torr inside the evaporator was maintained by a vacuum pump, and the flask rotated at a rate of 30 rpm. After the distillate was collected it was stored in a freezer. The residue remaining from the distillation was kept in the refrigerator (4° C.) for 3 days, then physically squeezed and filtered first through a sterile gauze, then through a 0.45 μm Millipore filter into a sterile bottle and stored in a freezer. Both the distillate and filtrate fractions ("CsA") contained the active agents. CsA was subjected to further purification as outlined below.

Example 2

Isolation of preferred purified active agent

The preferred isolation technique shown in Scheme 1 was used to isolate the preferred purified active agent from CsA.

This active fraction (200 mg) was subjected to flash silica gel chromatography as described in *J. Org. Chem.* 1978, 43, 2923 (45×2 cm, 1×id column, 17 g $SiO_2$ packed using a $CH_2Cl_2$ slurry) eluting with $CH_2Cl_2$ (80 mL, "F3-1"), $CH_2Cl_2$:$CH_3OH$ (100:2, 150 mL, "F3-2"), $CH_2Cl_2$:$CH_3OH$ (100:4, 200 mL, "F3-3" through "F3-6"), producing six fractions (F3-1 through F3-6). Fraction F3-3 (28 mg) was active; thin layer chromatography [TLC, $SiO_2$, $CH_2Cl_2$:$CH_3OH$ (10:0.6), $R_f$=0.52; $C_{18}$, $CH_3OH$:$H_2O$ (3:7), $R_f$=0.48] indicated a single main compound in this fraction. Recrystallization of this fraction from $CH_2Cl_2$:$CH_3OH$

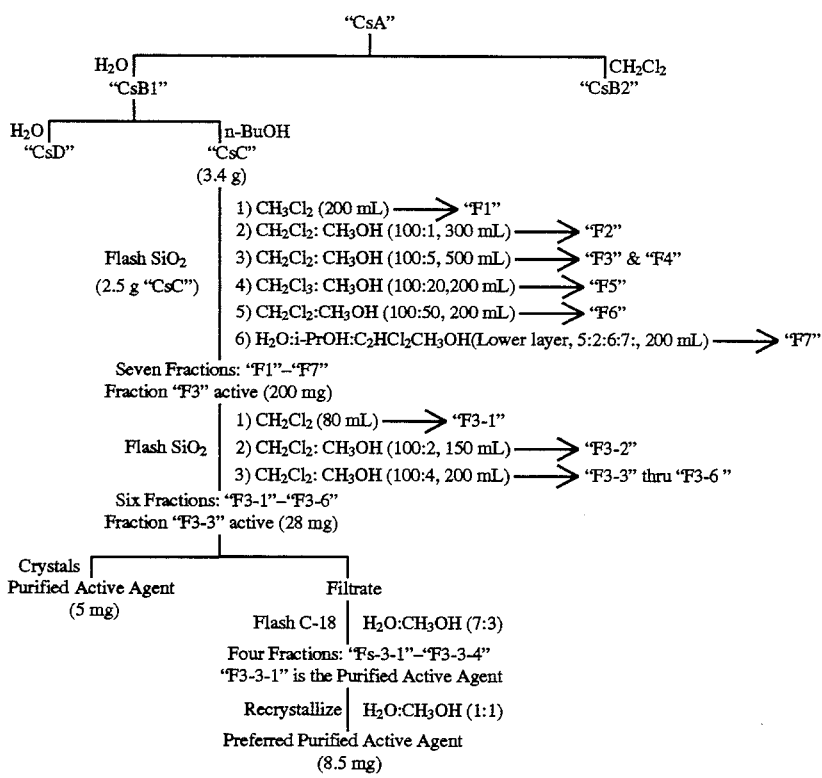

Scheme 1

CsA (approximately 2 L) was extracted three times with an equal volume of methylene chloride ($CH_2Cl_2$, 3×2 L, 6 L total) to provide the methylene chloride soluble fraction "CsB2". The aqueous layer "CsB1" was subsequently extracted four times with an equal volume of n-butanol (n-BuOH, 4×2 L, 8 L total) to provide the butanol soluble fraction "CsC", with the water soluble fraction "CsD" being the material remaining in the water layer. The solvents were removed from each fraction under reduced pressure on a rotary evaporator with a minimum amount of heating (<50° C.). The n-butanol fraction "CsC" (3.4 g from approximately 2 L of medicinal preparation) was active in the in vitro assays. A portion of "CsC" (2.5 g) was loaded onto a flash silica gel column (45×5 cm, 1×id, 100 g $SiO_2$ packed using a $CH_2Cl_2$ slurry) and the column was eluted to provide 7 fractions (F1–F7), eluting sequentially with $CH_2Cl_2$ (200 mL, "F1"), $CH_2Cl_2$:$CH_3OH$ (100:1, 300 mL, "F2"), $CH_2Cl_2$:$CH_3OH$ (100:5, 500 mL, "F3" and "F4"), $CH_2Cl_2$:$CH_3OH$ (100:20, 200 mL, "F5"), $CH_2Cl_2$:$CH_3OH$ (100:50, 200 mL, "F6"), and $H_2O$:i-PrOH:$CH_2Cl_2$:$CH_3OH$ (5:2:6:7, lower layer, 200 mL, "F7", i-PrOH=isopropanol). Fraction F3 was active in the in vitro bioassays.

(10:1, 0.75 mL) gave 11β,13-dihydrolactucin (5 mg). The filtrate, which TLC indicated was primarily 11β,13-dihydrolactucin, was chromatographed on a flash reversed phase $C_{18}$ column (45×1 cm, 1×id column, 5 g $C_{18}$ stationary phase packed using an $H_2O$:$CH_3OH$, 7:3 slurry) eluting with $H_2O$:$CH_3OH$ (7:3, 120 mL) to provide four fractions, F3-3-1 through F3-3-4. The first eluting fraction, F3-3-1 contained the 11β,13-dihydrolactucin. Recrystallization of this fraction from 50% aqueous methanol (0.5 mL) gave additional 11β,13-dihydrolactucin (8.5 mg). A total of 13.5 mg of 11β,13-dihydrolactucin was isolated in pure form from approximately 2 L of CsA.

All solvents were distilled prior to use. Flash silica gel (40–63 μm, 230–400 mesh) was purchased from EM Science (Gibbstown, N.J., U.S.A.). Column chromatography was monitored by thin layer chromatography using silica gel plates (aluminum-backed, silica gel type-G/UV, 250 μm thickness, Whatman, Hillsboro, Ore., U.S.A.) or $C_{18}$ reverse phase plates (glass-backed, Rp-18 F-254S, 250 μm thickness, EM Science) developing with the same eluant used to elute the column. Reverse phase $C_{18}$ stationary phase (40 μm) was purchased from J. T. Baker (Phillipsburg, N.J., U.S.A.).

Column chromatography was conducted, collecting the eluted solutions in test tubes, approximately 5–7 mL per tube. Fractions were then formed by selective combination of the solution in the tubes based upon TLC $R_f$'s:

Chromatography of "CsC" Producing Fractions "F3" through "F7":

Silica gel TLC plates, $CH_2Cl_2$:$CH_3OH$ (10:0.6). Each "spot" may or may not represent one compound.

"F1"—2 spots, $R_f$'s: 0.75, 0.70

"F2"—3 spots, $R_f$'s: 0.70, 0.60, 0.52

"F3"—3 spots, $R_f$'s: 0.60, 0.52, 0.38

"F4"—2 spots, $R_f$'s: 0.43, 0.38

"F5"—3 spots, $R_f$'s: 0.33, 0.28, 0.23

"F6"—1 spot, $R_f$: 0.20

"F7"—1 spot, $R_f$: 0.08

Chromatography of "F3-3" Producing Fractions "F3-1" through "F3-6":

Silica gel TLC plates, $CH_2Cl_2$:$CH_3OH$ (10:0.6). Each "spot" may or may not represent one compound.

"F3-1"—1 spot, $R_f$: 1.00

"F3-2"—2 spots, Rf's: 0.60, 0.52

"F3-3"—1 spot, $R_f$: 0.52

"F3-4"—2 spots, Rf's: 0.52, 0.43

"F3-5"—2 spots, Rf's: 0.08, 0.00

"F3-6"—1 spot, $R_f$: 0.00

The "preferred purified active agent" so isolated was subjected to identification analysis as described in Example 7.

Example 3

In vitro anticancer bioassays.

This example demonstrates how the scope of the anticancer activity of CsA was evaluated (Tables 2–10), and how the various fractions isolated as described in Example 2 were tested for in vitro anticancer activity. The in vitro activity observed with the $^3$H-thymidine incorporation assay (see below) was used to guide the isolation to the preferred purified active agent. Thus, when the extract CsA was separated into methylene chloride ("CsB2"), n-butanol ("CsC"), and water soluble ("CsD") fractions, each of these subfractions was tested in the $^3$H-thymidine incorporation assay (Table 4b), and the active fraction CsC was then subjected to further chromatographic purification as outlined in Scheme 1. Each of the subfractions obtained from the chromatography were then assayed in the $^3$H-thymidine incorporation screen, with the active fraction "F3" further purified. Ultimately the preferred purified active agent was obtained.

The in vitro anticancer bioassays used in this work are highly selective in uncovering the active fractions during purification. The results of the bioassays described in this Example were evaluated by comparing a variety of tumor and nontumor cell lines to avoid the misguidance of only one general cytotoxicity test, as well as to ascertain the selectivity level against minor and normal cell lines. The cell lines used are shown in Table 2.

TABLE 2

| Cell Lines Used in Bioassays | |
|---|---|
| Mouse-Derived Type B Lymphomas | Mouse-Derived Type T Lymphomas |
| LS | El-4 |
| LK | BW |

TABLE 2-continued

| Cell Lines Used in Bioassays | |
|---|---|
| M12 | YAC |
| TA3 | RDM-4 |
| Normal Cells | Other Cells |
| L929 (fibroblasts) | M Φ5 (macrophage tumor) |
| C7 (cloned T-cells) splenocytes | P815 (mastocytoma) |
| Colon Adenocarcinoma | SP2/0 (myeloma) |
| CT26 (mouse/colon) | |
| HT-29 (human/colon) | |
| CRL1616 (mouse/breast) | |

All cell lines and lymphocyte clones were obtained from the American Type Culture Collection (ATCC, Rockville, Md., U.S.A.), except CT26, which was obtained from Dr. Selwyn A. Broitman of Boston University as a gift from Dr. Michael Brattain, Birmingham Medical Center, Birmingham, Ala., U.S.A. Development of CT26 is described in Brattain, M. G. et al., *Cancer Research* 1980, 40, 2142–46.

The in vitro bioassays are described below; all tests were run at 37° C. Dosages in µg/mL in the Tables 5 and 6 refer to concentrations of residual solids obtained by evaporation in vacuo of solvent from CsA and the solubility subfractions (CsB1, CsB2, CsC, and CsD) reconstituted in aqueous solution.

1) The Trypan Blue Dye Exclusion Test for monitoring cell viability as described by Phillips, H. J., in *Tissue Culture Methods and Applications*; Kruse, P. F., Jr., Patterson, M. K., Eds.; Academic Press, New York, 1973, 406, and by Wu, Y. W., Chik, L. L., Knazek, R. A. *Cancer Research* 1989, 49, 3754. The results of this assay are expressed as a percentage of viable cells:

[% viable cells]=[no. of alive cells]/[total no. of cells]×100 where the total no. cells=dead cells+alive cells. The results are compared directly with an untreated control, which typically show a three-to-four-fold increase for cancer cells, and a two-fold increase for normal cells. Treatments resulting in [% viable cells] of <30% are considered cytotoxic. Therefore, the trypan blue dye exclusion test was used to assess the number of dead and alive cells using various cell lines upon treatment with the crude and purified agent. This test provides a simple clue to the acute or late onset of a cytotoxic response. Readings for this and all other in vitro assays were taken 48 hours after treatment with the unpurified agent, and also 48 hours after treatment for the purified agent. Thus, the trypan blue dye exclusion assay functions to confirm whether or not the cells were viable at the time readings were taken for other bioassays.

2) The $^3$H-Thymidine Incorporation Test as described by Ju, S. T., Dorf, M. E. *J. Immunol.* 1985, 134, 3722. This test was used for monitoring cellular proliferation by monitoring DNA synthesis. The results are expressed as percent $^3$H-thymidine incorporation relative to an untreated control:

[% $^3$H-thymidine incorporation]=[*cpm* agent treated cells]/[*cpm* untreated cells]×100 where cpm=counts per minute. Treatments resulting in [% $^3$H-thymidine incorporation] of <50% are considered active.

The $^3$H-thymidine incorporation assay therefore measures the amount of DNA synthesis when the cells are in the "S"

phase of the cell cycle, and is used to assess cell proliferation. Cancer cells, which have a very rapid cell cycle turnover, normally incorporate large amounts of tritium ($^3$H) unless inhibited by an exogenous agent. With these inhibitory treatments, the incorporation of tritium into DNA (i.e. DNA synthesis) is greatly reduced. While the trypan blue dye exclusion test is an indicator of cell death, the $^3$H-thymidine incorporation test indicates a cytostatic status (not necessarily cytotoxic) of the cell. As previously noted, this latter test was the primary screen used to guide the isolation to the active agent.

3) $^{35}$S-Methionine Incorporation Test as described by Sorenson, C. M., Barry, M. A., Eastman, A. *J. Natl. Canc. Inst.* 1990, 82, 749. The results are expressed as percent $^{35}$S-methionine incorporation relative to an untreated control:

[% $^{35}$S-methionine incorporation]=[cpm agent treated cells]/[cpm untreated cells]×100 where cpm=counts per minute. Treatments resulting in [% $^{35}$S-methionine incorporation] of <50% are considered active.

The $^{35}$S-methionine incorporation test therefore measures protein synthesis. Activity in this bioassay could arise from inhibition of transcription and/or translation.

4) The DNA Fragmentation Assay as described by Ucher, D. S., Ashwell, J. D., Nichas, G. *J. Immunol.* 1989, 143, line, good activity against the BW and P815 cell lines, and weak activity against the LK and EL-4 cell lines, the latter of which is a very aggressive type T lymphoma tumor line. Most significant was the little or no inhibition of normal L929 fibroblast cell proliferation (Table 3).

TABLE 3

Trypan Blue Cell Viability Assay with Fraction CsA.[a,b]

| Cell Lines | LS | EL-4 | BW | LK | P815 | L929 |
|---|---|---|---|---|---|---|
| cell viability % | 4 | 55 | 34 | 51 | 34 | 79 |

[a] All tests were run with 250 μL/mL of CsA extract prepared as described in Example 1. The concentration of residual solids in CsA was approximately 2 mg/mL.
[b] 99+% viability is the control value (untreated cells).

These results were mirrored in the $^3$H-thymidine incorporation assays, which were expanded to include the CT26 and HT-29 adenocarcinoma lines. In these experiments, good to excellent inhibition of DNA synthesis was observed against all cell lines tested including the colon and breast adenocarcinoma lines, except for the EL-4 and fibroblast (L929) lines (Table 4).

TABLE 4

$^3$H-Thymidine Incorporation (DNA Synthesis) Inhibition with CsA.[a,b]

| | Cell Lines | | | | | | | | |
|---|---|---|---|---|---|---|---|---|---|
| | LS | EL-4 | BW | LK | P815 | L929 | CT26 | HT-29 | CRL1616 |
| $^3$H-Thymidine Incorp. % | 1 | 70 | 1 | 3 | 9 | 80 | 23 | 14 | 18 |
| cpm control[b] | 94,300 | 40,500 | 73,100 | 95,100 | 55,100 | 44,500 | 10,900 | 27,100 | 22,400 |

[a] All tests were run with 250 μL/mL of CsA extract prepared as described in Example 1. The concentration of residual solids in CsA was approximately 2 mg/mL.
[b] Control = untreated cells.

3461, and by Shi, Y., Szalay, M. G., Pasher, L., Boyer, M., Singh, B., Green, D. R. *J. Immunol.* 1990, 144, 3326. The DNA fragmentation assay uses $^3$H-thymidine labelled DNA and the results are expressed as percent specific DNA fragmentation relative to a control treated with pancreatic DNAase:

[% activity]=([cpm agent treated cells]−[background cpm])/{[(cpm DNAase treated cells)/2]−[background cpm]}×100 where cpm=counts per minute. In the absence of a DNA fragmenting agent or DNAase, the activity levels would be <10%. Treatments resulting in [% activity] of >50% are considered active. The results of the DNA fragmentation test therefore measure the amount of DNA cleavage induced by the agent, thereby revealing apoptosis or programmed cell death.

A. Bioassay Results: CsA

Initial experiments were conducted using the CsA in both the trypan blue and $^3$H-thymidine incorporation assays to survey the cytotoxicity/cytostatic nature of the agent, as well as the selectivity toward specific cell lines. Both assays revealed significant activity against a variety of cell lines (Tables 3 and 4). The trypan blue assay showed excellent activity against the mouse-derived type B lymphoma LS cell The results from these two assays were crucial in illustrating both the selective and the noncytotoxic nature of the active agent. Foremost was the little or no activity against the fibroblast cells L929, which contrasts dramatically with the activity observed against all cancer cell lines tested. This result strongly suggests that a potentially significant therapeutic window exists for this agent in treating neoplastic disorders. Next, the range of activities against the cancer cell lines indicates the selective nature of the agent. Finally, the strong inhibition against DNA synthesis shown toward all the cancer cell lines except EL-4 (Table 4, with a very notable lack of effect against the fibroblast L929 line) should be compared with the trypan blue cell viability assay (Table 3). The modest to weak activity in the trypan blue assay toward the BW, P815, LK and EL-4 cell lines is in stark contrast to the moderate to very strong activity against the same cell lines in the $^3$H-thymidine incorporation assay, indicating that the active agent is not cytotoxic, but is very effective in preventing proliferation. This noncytotoxic effect of the active agent is most likely the key to the selectivity observed, which in turn results in the potentially large therapeutic window. In contrast, a generally cytotoxic agent, such as a compound bearing the α,β-unsaturated γ-lactone would have shown cell viability and $^3$H-thymidine incorporation results of <10% for all cell lines tested.

Figure 1B:
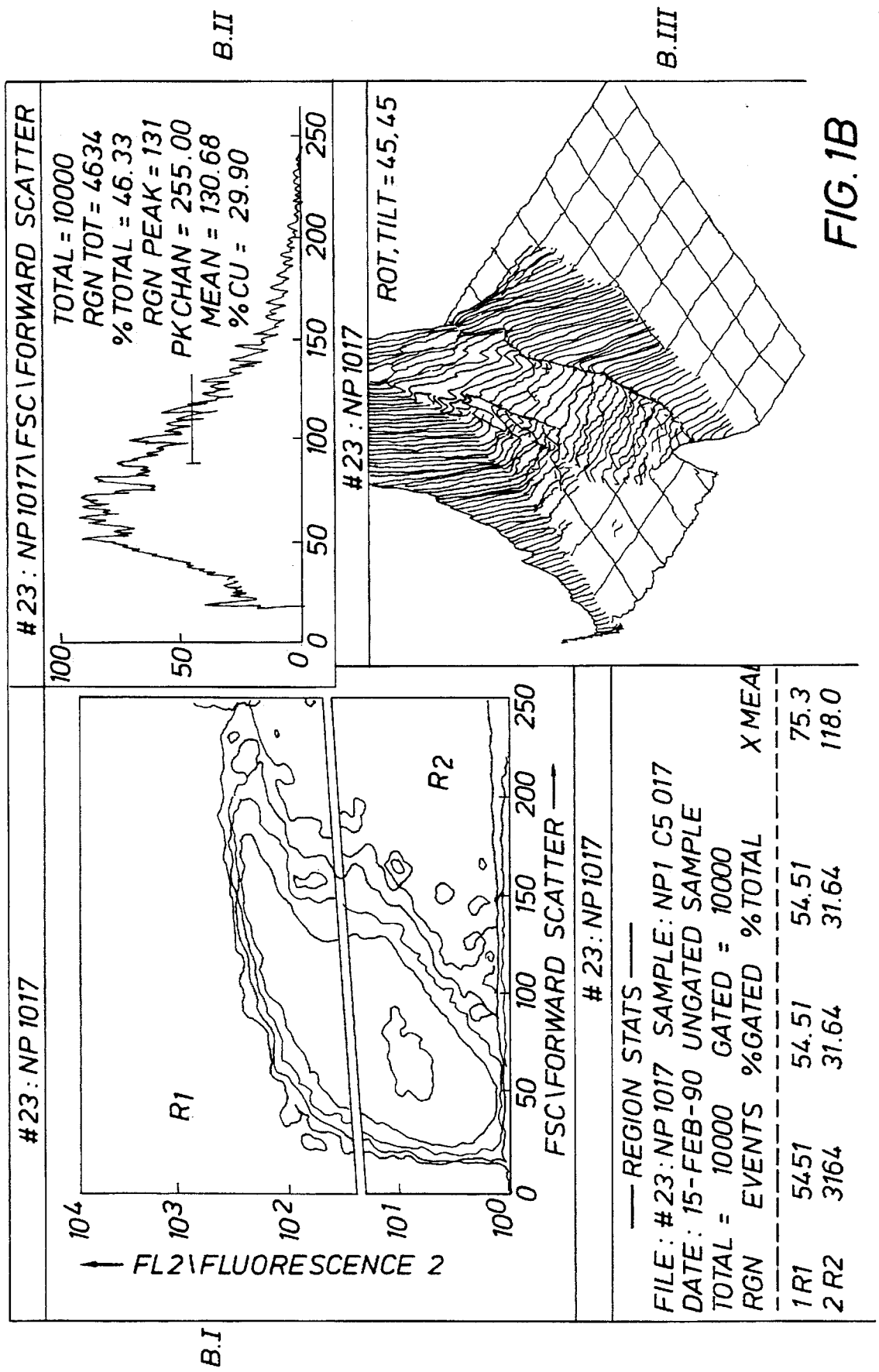

In order to confirm the noncytotoxic nature of CsA, a Fluorescence Activated Cell Sorting (FACS) screening test as described by Ackermann, M. F., Lamm, K. R., Wiegand, G. W., Luster, M. I. *Cancer Res.* 1989, 49, 528; and Ross, D. D., Jonesckis, C. C., Ordonez, J. V., Sisk, A. M., Wu, R. K., Hamburger, A. W., Nore, R. E. *Cancer Res.* 1989, 49, 3776, was used to show histograms of dead and living cells (FIG. 1). In this test, P815 mastocytoma cells were incubated with CsA extract for 18 hours in a standard tissue culture incubator (pH 7.34, 37° C., 10% carbon dioxide). Cell viability was assessed by flow cytometric measurement of cellular fluorescence after staining with propidium iodide in an isotonic solution (specific for dead cells) as described in the references cited above (Ackermann et al., and Ross et al.). This analysis reveals both cell death as well as cell damage as indicated by cell density. FIG. 1 shows the histograms of P815 cells with 50 µL/mL (FIG. 1A) and 500 µL/mL (FIG. 1B) of the extract CsA. The results of each screening test are presented in three plots. The upper left plot of each (FIGS. 1A.I and 1B.I) is a contour log graph of fluorescence intensity with the x-axis representing cell size and the y-axis representing cell optical density. A line divides this graph into two regions: R1, which shows dead cells, and R2, which shows dying cells (detected from the incorporation of propidium iodide). The graph in the upper right of each histogram (FIGS. 1A.II and 1B.II) is the x-axis fluorescence intensity vs. number of events, which represents the number of dead cells. The lower right plots (FIGS. 1A-III and 1B-III) are three dimensional plots of the data from the upper right graphs. In this manner, cell viability was quantitated from the FACS screens, and the expected decrease in cell viability with increasing dose of CsA was observed.

The results of the FACS screens indicated the essential dose/response relation subsequently confirmed with additional $^3$H-thymidine incorporation tests (Table 5b).

These results from the trypan blue and $^3$H-thymidine incorporation inhibition assays screens confirmed that the crude extract CsA was active against tumor cells (inhibited proliferation) without being cytotoxic.

B. Bioassay Results: Solubility Subfractions from CsA

With these preliminary results in hand, the crude aqueous preparation CsA was fractionated on the basis of solubility into methylene chloride ("CsB2"), n-butanol ("CsC"), and water ("CsD") soluble fractions according to Scheme 1 (see above), the initial steps for the isolation of the active agent in pure form. Each of these three fractions were then tested in the trypan blue and $^3$H-thymidine incorporation assays along with the original CsA as a control, against the LS cell line, which was the most sensitive of the cancer lines (Tables 3 and 4). At this stage, cloned T-cells (C7) and splenocytes (mouse-derived) were also included in the tests since the very encouraging lack of activity against the fibroblast L929 cells suggested a good therapeutic window. This window would be most effective if the agent was not cytotoxic, nor antiproliferative against T-cells and splenocytes. Finally, CsA as well as the three solubility fractions CsB2, CsC, and CsD, were also tested at decreasing concentrations in order to ascertain a dose-response relation. The results of the trypan blue and $^3$H-thymidine incorporation assays against the three cell lines are compiled in Tables 5a–5f. In these assays, exact concentrations of the residual solids obtained from evaporation of the individual solutions CsA, CsB1, CsB2, CsC, and CsD were employed.

TABLE 5a

Trypan Blue Cell Viability (%) Assay Using LS Cancer Cell Line.[a]

| Fractions | CsA | CsB2 | CsC | CsD |
|---|---|---|---|---|
| Dosage (µg/mL) | | | | |
| 25 | 100 | 100 | 100 | 100 |
| 50 | 95 | 95 | 95 | 95 |
| 75 | 85 | 85 | 85 | 85 |
| 100 | 75 | 75 | 75 | 75 |
| 250 | 60 | 60 | 60 | 60 |

[a]99+% viability is the control value (untreated cells).

TABLE 5b $^3$H-Thymidine Incorporation (DNA Synthesis) Inhibition (%) Using LS Cancer Cell Lines.[a]

| Fractions | CsA | CsB2 | CsC | CsD |
|---|---|---|---|---|
| Dosage (µg/mL) | | | | |
| 25 | 20 | 50 | 5 | 100 |
| 50 | 5 | 40 | 2 | 100 |
| 75 | 2 | 35 | 2 | 100 |
| 100 | 2 | 28 | 2 | 100 |
| 250 | 2 | 25 | 2 | 50 |

[a]Total cpm of the untreated cells was: 105,000.

TABLE 5c

Trypan Blue Cell Viability (%) Assay Using C7 Cloned T-Cells.[a]

| Fractions | CsA | CsB2 | CsC | CsD |
|---|---|---|---|---|
| Dosage (µg/mL) | | | | |
| 25 | 85 | 85 | 85 | 85 |
| 50 | 70 | 75 | 70 | 70 |
| 100 | 30 | 60 | 30 | 30 |

[a]99+% viability is the control value (untreated cells).

TABLE 5d $^3$H-Thymidine Incorporation (DNA Synthesis) Inhibition (%) Using C7 Cloned T-Cells.[a]

| Fractions | CsA | CsB2 | CsC | CsD |
|---|---|---|---|---|
| Dosage (µg/mL) | | | | |
| 25 | 75 | 95 | 60 | 60 |
| 50 | 60 | 80 | 30 | 30 |
| 100 | 38 | 50 | 25 | 25 |

[a]Total cpm of the untreated cells was: 1,500.

TABLE 5e

Trypan Blue Cell Viability (%) Assay Using Splenocytes.[a]

| Fractions | CsA | CsB2 | CsC | CsD |
|---|---|---|---|---|
| Dosage (µg/mL) | | | | |
| 25 | 87 | 87 | 85 | 85 |
| 50 | 80 | 80 | 75 | 75 |
| 100 | 30 | 75 | 30 | 30 |

[a]99+% viability is the control value (untreated cells).

TABLE 5f $^3$H-Thymidine Incorporation (DNA Synthesis) Inhibition (%) Using Splenocytes.[a]

| Fractions | CsA | CsB2 | CsC | CsD |
|---|---|---|---|---|
| Dosage (µg/mL) | | | | |
| 25 | 85 | 85 | 50 | 50 |
| 50 | 60 | 60 | 25 | 25 |
| 100 | 36 | 36 | 5 | 5 |

[a]Total cpm of the untreated cells was: 5,000.

Comparison of the data in Tables 5a and 5b again indicated that the agent prevents proliferation of cancer cells (LS cell line) without being cytotoxic. Moreover, this activity was found primarily in the n-butanol soluble fraction "CsC", indicating that successful partitioning of the active agent on the basis of solubility had occurred (Table 5b). As expected, the inhibition of $^3$H-thymidine incorporation increased as the active agent was concentrated in the n-butanol soluble fraction CsC (Table 5b), with the dose/response relation originally observed with CsA being maintained after fractionation. Finally, Tables 5c–5f indicate that there is little effect on cloned T-cells or splenocytes at concentrations that are very effective against the LS cancer cell line (25 and 50 µg/mL).

In addition to the results locating the anticancer activity in solubility fraction CsC, preliminary bioassays were run on the initial water fraction CsB1, from which the solubility fraction CsC was derived, in order to examine the effect of the extract on DNA fragmentation and membrane puncturing (chromium release). Exceptionally high activity was observed with CsB1 treated cells in both the DNA fragmentation (Table 6) and the chromium release (Table 7) assays. Significant activity (>50% relative to fragmentation induced by DNAase) was induced by CsB1 against several lines, with the activity against the Type B lymphoma M12 exceeding the fragmentation induced by DNAase itself (163%). Most importantly, only negligible fragmentation was induced in the L929 fibroblast cells (6%).

With the active fraction from the partitioning of CsA identified as the n-butanol soluble fraction CsC, the isolation of the active agent proceeded through two sequential flash silica gel chromatography columns and a recrystallization to obtain the preferred purified active agent 11β,13-dihydrolactucin. The $^3$H-thymidine incorporation assay using the LS cell line was applied to each fraction produced chromatographically (Scheme 1) and in the recrystallization to identify this compound as the active agent.

C. Bioassays Results: Preferred Purified Active Agent, 11β,13-dihydrolactucin

With the preferred purified active agent in hand, $^3$H-thymidine incorporation and trypan blue assays were initially performed at different dosages using LK and BW lymphoma cell lines in order to confirm the activity of the preferred purified active agent, and to bracket the active concentration range for the preferred purified active agent. With a molecular weight of 328, a 1 µg/mL solution corresponds to 3 µM concentration. In addition, the time course of cell viability in the trypan blue assay was also monitored in order to best optimize subsequent assays to ensure that the cells were still viable at the time of measurement, and to ensure a nontoxic response of the cells to the agent. Toxicity of the agent would have been observed as cell death within 2 hours. The trypan blue assays (Table 7), run at 30 µM and 3 µM of purified agent (10 and 1 µg/mL, respectively), indicated excellent cell viability after 24 hours, though with a significant drop in viability after 48 hours at a 30 µM dose of preferred purified active agent. Consequently the results of the in vitro assays employing purified agent were all recorded after 24 hours. In the $^3$H-thymidine incorporation assay (Table 8), dosages ranging from 0.1 to 250 µg/mL were examined. These results indicated a good dose/response relation with ED$_{50}$ in the micromolar range.

TABLE 7

Trypan Blue Cell Viability (%) Assay with Preferred Purified Active Agent.[a]

| | LK Cells | | BW Cells | |
|---|---|---|---|---|
| Time (Hours) | 10 µg/mL | 1 µg/mL | 10 µg/mL | 1 µg/mL |
| 2 | 100 | 100 | 100 | 100 |
| 5 | 100 | 100 | 100 | 100 |
| 12 | 100 | 100 | 100 | 100 |
| 24 | 85 | 100 | 85 | 100 |
| 36 | 72 | 90 | 72 | 90 |
| 48 | 60 | 90 | 60 | 90 |

[a]99+% viability is the control value (untreated cells).

TABLE 6

DNA Fragmentation Induced by Aqueous Fraction CsB1.[a]

| Cell Line | L929 | LS | CT26 | LK | M12 | TA3 | SP2/0 | MΦ5 |
|---|---|---|---|---|---|---|---|---|
| Fragmentation[b] % | 6 | 58 | 37 | 40 | 163 | 77 | 63 | 52 |
| cpm control[c] | 50,100 | 60,000 | 96,400 | 74,400 | 94,900 | 68,700 | 30,600 | 120,000 |

[a]All tests were run with 100 µg/mL.
[b]Relative to fragmentation induced by pancreatic DNAase.
[c]Control = untreated cells.

TABLE 8

$^3$H-Thymidine Incorporation (DNA Synthesis) Inhibition (%) of Preferred Purified Active Agent.[a]

| Cell Lines | LK | BW |
|---|---|---|
| Dosage (µg/mL) | | |
| 0.1 | 95 | 90 |
| 1 | 75 | 50 |
| 10 | 5 | 40 |
| 25 | 2 | 25 |

TABLE 8-continued $^3$H-Thymidine Incorporation (DNA Synthesis) Inhibition (%) of Preferred Purified Active Agent.[a]

| Cell Lines | LK | BW |
|---|---|---|
| 100 | 2 | 20 |
| 250 | 2 | 5 |

[a]Total cpm for untreated cells was 115,000 for LK cells, 5,000 for BW cells.

The final in vitro assays performed with the preferred purified active agent were intended to examine the scope of the activity in the trypan blue assay against a wider range of tumor cell lines (Tables 10 and 11). These cell lines included a Type B lymphoma BW8767, a BW mutant which is more resistant than the BW cell lines used in other assays, as evidenced by the results in Tables 10 and 11.

TABLE 10

$^3$H-Thymidine Incorporation (DNA Synthesis) Inhibition (%) with Preferred Purified Active Agent Against Various Cell Lines.

| Cells | CT26 | BW5147[a] | P815 | EL-4 | RDM-4 | BW8767[a] | C7 |
|---|---|---|---|---|---|---|---|
| Dosage (µg/mL) | | | | | | | |
| 0.1 | 100 | 100 | 100 | 100 | 100 | 100 | 100 |
| 0.5 | 50 | 100 | 100 | 100 | 100 | 100 | 100 |
| 1.0 | 5 | 45 | 50 | 78 | 80 | 80 | 100 |
| 10 | 1 | 25 | 36 | 38 | 60 | 60 | 75 |
| cpm comtrol[b] | 28,000 | 20,000 | 20,000 | 2,500 | 11,000 | 30,000 | 1,800 |

[a]The BW5147 cell line is the same as the BW cell line used in all other in vitro assays. The numbers given here distinguish it from the mutant resistant line BW8767.
[b]Control = untreated cells.

The ability of the preferred purified active agent to inhibit cell proliferation without a cytotoxic effect was also clearly revealed in the $^{35}$S-methionine incorporation test which monitors protein synthesis. In this test, BW and LK lymphoma cells were treated with the preferred purified active agent at 1 µg/mL and 10 µg/mL for comparison with an untreated control. The treated cells were split into two groups, one of which was thoroughly washed to remove the preferred purified active agent prior to incubation with $^{35}$S-methionine. The results (Table 9) indicated significant inhibition of protein synthesis (and therefore cell proliferation) against both cell lines upon treatment with only 1 µg/mL of preferred purified active agent (a concentration at which both cell lines were completely viable after 24 hours, and 90% viable after 48 hours, Table 7) in the unwashed group. Removal of the preferred purified active agent by washing, however, completely restored the ability of the cancer cells to synthesize proteins, demonstrating the irreversible noncytotoxicity at the preferred purified active agent.

TABLE 9

$^{35}$S-Methionine Incorporation (Protein Synthesis) Inhibition by Preferred Purified Active Agent.[a]

| | $^{35}$S-Methionine Incorporation | | | |
|---|---|---|---|---|
| Dosage (µg/mL) | BW | BW (washed) | LK | LK (washed) |
| 1 | 10 | 100 | 50 | 100 |
| 10 | 2 | 100 | 10 | 100 |

[a]Total cpm of the untreated cells was 201,000 for BW cells, 366,000 for LK cells.

TABLE 11

Trypan Blue Cell Viability (%) Assay with Purified Active Agent Against Various Cell Lines.[a]

| Cells | CT26 | BW5147[b] | P815 | EL-4 | RDM-4 | BW8767 | C7 |
|---|---|---|---|---|---|---|---|
| Dosage (µg/mL) | | | | | | | |
| 0.1 | 100 | 100 | 100 | 100 | 100 | 100 | 100 |
| 0.5 | 100 | 100 | 100 | 100 | 100 | 100 | 100 |
| 1.0 | 100 | 100 | 100 | 100 | 100 | 100 | 100 |
| 10 | 100 | 80 | 80 | 100 | 90 | 100 | 90 |

[a]100% viability is the control value (untreated cells).
[b]The BW5147 cell line is the same as the BW cell line used in all other in vitro assays. The numbers given here distinguish it from the mutant resistant line BW8767.

In summary, the in vitro assays beginning with the crude medicinal preparation CsA, through the isolation fractions to the preferred purified active agent 11β,13-dihydrolactucin, indicated an excellent level of antineoplastic activity against a variety of cell lines. This activity was highly selective in that little or no activity was observed against fibroblast cells (L929), cloned T-cells, or splenocytes, indicating a potentially large therapeutic window. Most importantly, the antineoplastic activity was not associated with cytotoxicity, but rather a prevention of cancer cell proliferation. This indeed may be the basis of the selectivity since cytotoxicity is usually very general.

Example 4

In vivo activity.

This Example demonstrates in vivo efficacy of the active agents of the present invention. The in vivo activity of the active agent was assessed against two tumor cell types injected into mice: CT26 and Ehrlich Ascites (EAT) tumor cell lines. The protocols of the "National Cancer Institute, Drug Research and Development Division of Cancer Treatment, Instruction 14, Screening Data Summary Interpretation and Outline of Current Screen" were followed.

1. Implantation of Ehrlich Ascites tumor cells into BALB/C mice.

Figure 2:
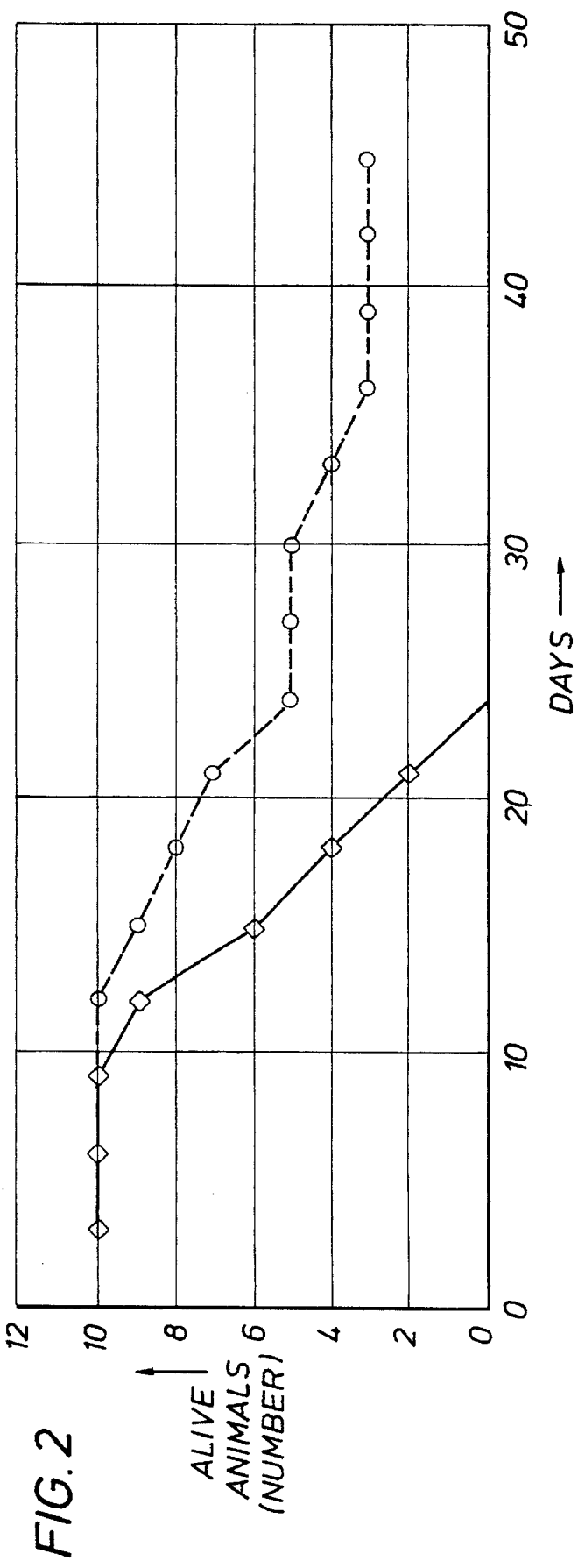
FIG. 2 is the survival graph for BALB/C mice implanted with Ehrlich Ascites tumor cells.

Ehrlich-Ascites tumor (EAT) cells (about $1 \times 10^5$ cells per mouse) were injected intraperitoneally into male BALB/C mice. Ten mice were treated every five days with 0.5 ml of CsA (1.0 mg of solids/mouse) while a control group of 10 mice were injected with PBS. The CsA-treated group had prolonged survival compared to the control group, (treated group/control group)>120%. Three of the treated mice were completely cured (i.e., no evidence of EAT tumor cells as evidenced by survival, FIG. 2). In FIG. 2, "+" represents the survival of the control mice and "." represents the survival of the treated mice. The weight gain of the treated mice relative to the control was >140% as established by NCI protocols.

2. Weight Gain and White Blood Cell Counts.

The NCI protocol for weight gain mentioned above of (treated group)/(untreated group)>140%, is important since this eliminates weight gain as a consequence of tumor growth as a positive phenomenon. While the weight gain of the CsA treated BALB/C mice in the implantation of Ehrlich Ascites tumor cell studies fell within this weight gain protocol, the weight gain observed in the treated mice was different than that usually observed, since the tumors had regressed. In order to establish that this weight gain in the treated mice was a direct effect of CsA, a separate experiment was conducted using two additional groups of ten BALB/C mice each. The first group of ten mice was treated every five days with 0.5 mL of CsA aqueous solution (1.0 mg of CsA solids per mouse) while the second group was treated with PBS as a control. The CsA treated mice gained weight relative to the control group ($p<0.1\%$, Table 12). White blood cell counts of the same two groups were also measured, and the CsA treated group had higher counts ($p<0.1\%$) than the control group (Table 13).

TABLE 12

Average Weight Gain in Mice with CsA Treatment

Average Weight in Grams of Ten Mice

| Days | 0 | 5 | 10 | 15 | 20 |
|---|---|---|---|---|---|
| Control | 23 | 24.7 | 25.2 | 25.6 | 26 |
| Treated | 24 | 26.2 | 27.5 | 29.2 | 33 |
| S.E.M. | 0.321 | 0.817 | 0.854 | 0.801 | 0.490 |

TABLE 13

White Blood Cell Counts in Mice Treated with CsA

Average White Blood Cell Counts of Ten Mice

| Days | 0 | 5 | 10 | 15 | 20 |
|---|---|---|---|---|---|
| Control | 7300 | 8000 | 9000 | 8600 | 9200 |
| Treated | 8000 | 8500 | 10500 | 17000 | 20500 |
| S.D. | 890.3 | 1014.2 | 2451.5 | 2087.2 | 2856.4 |

The results of these experiments showed that CsA directly increased weight and white blood cell counts, further supporting the conclusion that CsA is not cytotoxic. Typically, administration of a cytotoxic agent would result in weight loss under these conditions.

3. Metastases in Lungs of BALB/C Mice Injected with CT26 Colon Adenocarcinoma Cells: First Study.

For the in vivo experiment using CT26 colon adenocarcinoma cell line, tumor cells (about $1 \times 10^5$ per mouse) were injected into the tail veins of male BALB/C mice. The mice were split into four groups: a control group of four mice, an endotoxin group of 3 mice, a test group of five mice treated on day 0 with 0.5 mL of CsA, and a test group of five mice treated on day 5 with 0.5 mL of CsA. Animals were sacrificed on day 26 and the metastases in the lung (the first destination of CT26 colon adenocarcinoma) were counted. The results are presented in Table 14, indicating the low level of metastases ($p<2\%$) in the two extract treated mice. All animals in the test groups which received CsA were in good health and gained weight during the test period. Furthermore, the metastases size in the control group were large (on the order of 85 mm in diameter), while the metastases in the two test groups treated with CsA were only small points. The endotoxin level of CsA with the "Limulus ameobocyte lysate" (LAL) method was <0.0025 ng/mL (limit of detection); $LD_{50}$ was 1.65 mL/23 g mouse.

Sometimes natural products, although they are sterilized, may contain minimal amounts of endotoxin. On rare occasions, it is claimed that endotoxin may inhibit tumor growth, behaving as a tumor necrotizing factor. The animals were injected with a minimal dose (400 nanograms per ml, equivalent to the amount in the natural product, 2 microgram *E. coli* 055:B5 lipopolysaccharide standardized against USP Reference Standard Endotoxin (RSE); endotoxin units per microgram range between 5,000–20,000) of endotoxin (Sigma Chemical Co., St. Louis, Mo., U.S.A.). This amount was not enough to affect the mice clinically (such as causing endotoxemia).

TABLE 14

Metastases in Lungs of BALB/C Mice Injected with CT26 Colon Adenocarcinoma Cells*

| Control Group | Endotoxin Group | Test Group Day 0 | Test Group Day 5 |
|---|---|---|---|
| 14 | 60 | 11 | 12 |
| 89 | 20 | 2 | 0 |
| 97 | 66 | 59 | 4 |
| 88 | | 2 | 18 |
| | | 42 | 9 |
| Mean ± S.D.: 72.0 ± 19.4 | Mean ± S.D.: 48.6 ± 14.4 | Mean ± S.D.: 23.2 ± 11.6 | Mean ± S.D.: 8.6 ± 3.1 |

*Data are given as the number of metastases per individual mouse.

4. Metastases in Lungs of BALB/C Mice Injected with CT26 Colon Adenocarcinoma Cells: 2nd Study.

In a second study using more mice, tumor cells were injected into the tail veins of male BALB/C mice as before. The mice were split into 4 groups with 17 mice in each group: a control group treated with PBS, an endotoxin group, a test group treated on day 0 with CsA (0.5 mL) and a test group treated on day 5 with CsA (0.5 mL). Animals were sacrificed on day 26 and the number of lung metastasis counted (Table 15). All animals in the two test groups which received CsA were in good health and gained weight (>140%) during the test period. The endotoxin level of the extract with the "Limulus Amoebocyte Lysate (LAL)" method was <0.0025 ng/mL ($p<0.1\%$). The $LD_{50}$ was 2 mg/23 g mouse. As noted in the previous study, the metastases size in the control group were large (~85 mm in diameter), while the metastases in the two test groups treated with CsA were only small points.

TABLE 15

Metastases in Lungs of BALB/C Mice Injected with CT26 Adenocarcinoma Cells.

| Control Group | Endotoxin Group | Test Group Day 0 | Test Group Day 5 |
|---|---|---|---|
| 49 | 60 | 11 | 10 |
| 86 | 51 | 30 | 0 |
| 99 | 60 | 14 | 0 |
| 75 | 75 | 7 | 3 |
| 83 | 55 | 3 | 18 |
| 78 | 54 | 6 | 8 |
| 78 | 80 | 15 | 7 |
| 92 | 86 | 12 | 6 |
| 69 | 76 | 4 | 4 |
| 60 | 82 | 2 | 15 |
| 86 | 72 | 12 | 0 |
| 90 | 90 | 10 | 0 |
| 82 | 84 | 22 | 8 |
| 64 | 68 | 4 | 8 |
| 94 | 78 | 3 | 15 |
| 80 | 82 | 11 | 4 |
| 75 | 69 | 11 | 5 |
| Mean ± S.D.: 78.8 ± 3.1 | Mean ± S.D.: 71.9 ± 2.9 | Mean ± S.D.: 10.4 ± 1.8 | Mean ± S.D.: 6.5 ± 1.3 |

5. Metastases in Lungs of BALB/C Mice Injected with CT26 Colon Adenocarcinoma Cells: 3rd Study In a subsequent experiment, mice that had been implanted with CT26 cells as above were treated on day 5 with the solid residue from the evaporation of CsA (100 μg/g mouse), and with the preferred purified active agent 11β,13-dihydrolactucin (5 μg/g mouse). Results shown in Table 16 demonstrate that all treated groups had fewer metastases (<0.1%).

TABLE 16

Metastases in Lungs of BALB/C Mice Injected with CT26 Colon Adenocarcinoma Cells: 3rd Study[a]

| Treatment | Number of Metastases (mean ± S.D.) |
|---|---|
| Control | 45.3 ± 3.7 |
| CsA | 7 ± 2.041 |
| 11β, 13-dihydrolactucin | 0.33 ± 0.33 |

[a] Five mice per group.

Example 6

Human Treatment.

The patient was a 42-year old male diagnosed as being in the final stages of lung cancer and confined to bed (stage 4, oat cell carcinoma). He had advanced metastases to the lymph nodes, and poor prognosis with a life expectancy of about one month. The patient was administered CsA beginning in September 1991. He received about three to four fluid ounces (equal to about 2 mg/mL of hindaba extract CsA) three times a day. Shortly after treatment commenced, his lymph node tumors had noticeably shrunk as determined by multiple biopsies and X-rays, and the lung cancer remitted. After one month of beginning treatment, the patient started exercising, gained weight, and returned to work. Treatment continued until the patient later died of unnatural causes unrelated to cancer in June of 1992.

Example 7

Identification of the Preferred Purified Active Agent.

This Example demonstrates the techniques used to identify the preferred purified active agent, the structure of which is:

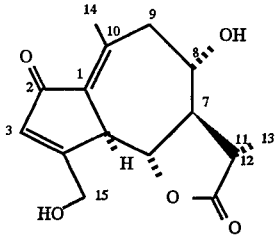

Figure 3:
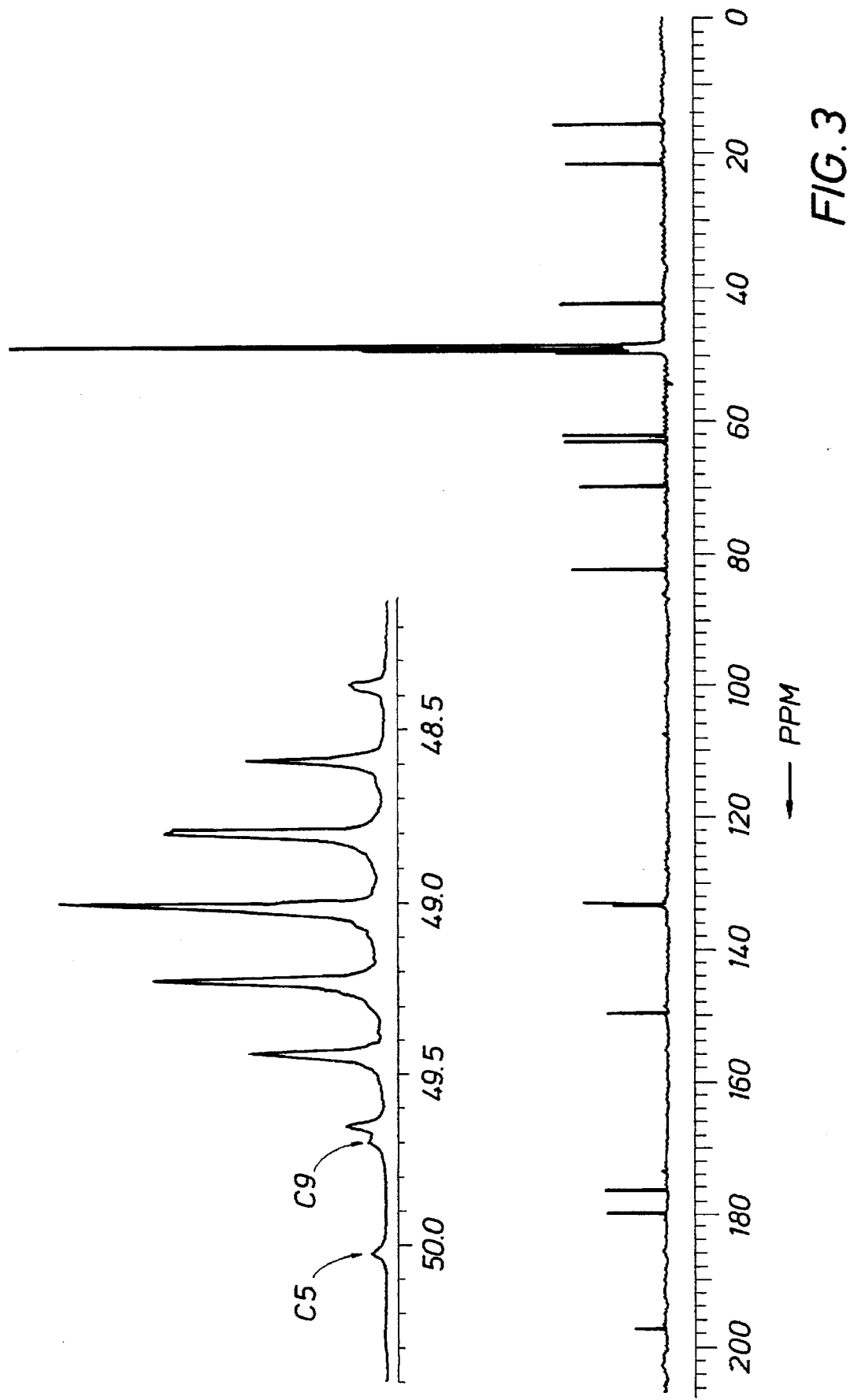
FIG. 3 depicts $^{13}$C NMR spectra of the purified active agent of the present invention in $CD_3OD$.

The structure determination of the preferred purified active agent isolated as described in Example 2 relied on spectroscopic methods, primarily $^1$H and $^{13}$C NMR spectroscopy in $CD_3OD$, supported by IR, MS, and UV data. The presence of fifteen carbons in the $^{13}$C NMR spectrum (FIG. 3), one of which was located within the solvent multiplet at δ 49.7 (FIG. 3 inset), included a conjugated ketone carbonyl (δ 197.4) and a second carbonyl tentatively assigned to a gamma-lactone carbonyl (δ 180.0), suggesting a sesquiterpene lactone.

Figure 4A:
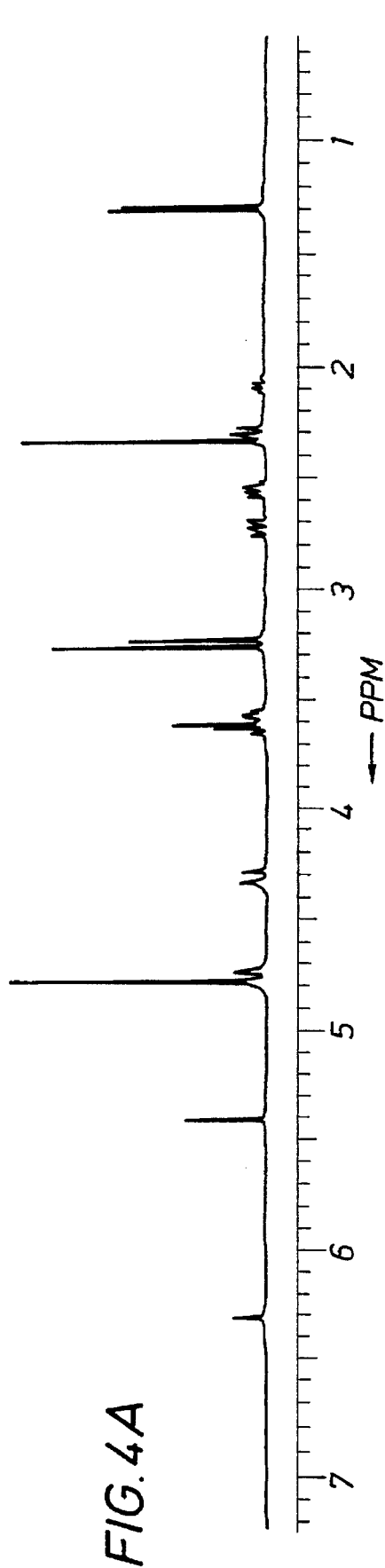
FIG. 4 depicts $^1$H NMR spectra of the purified active agent in $CD_3OD$.
Figure 4B:
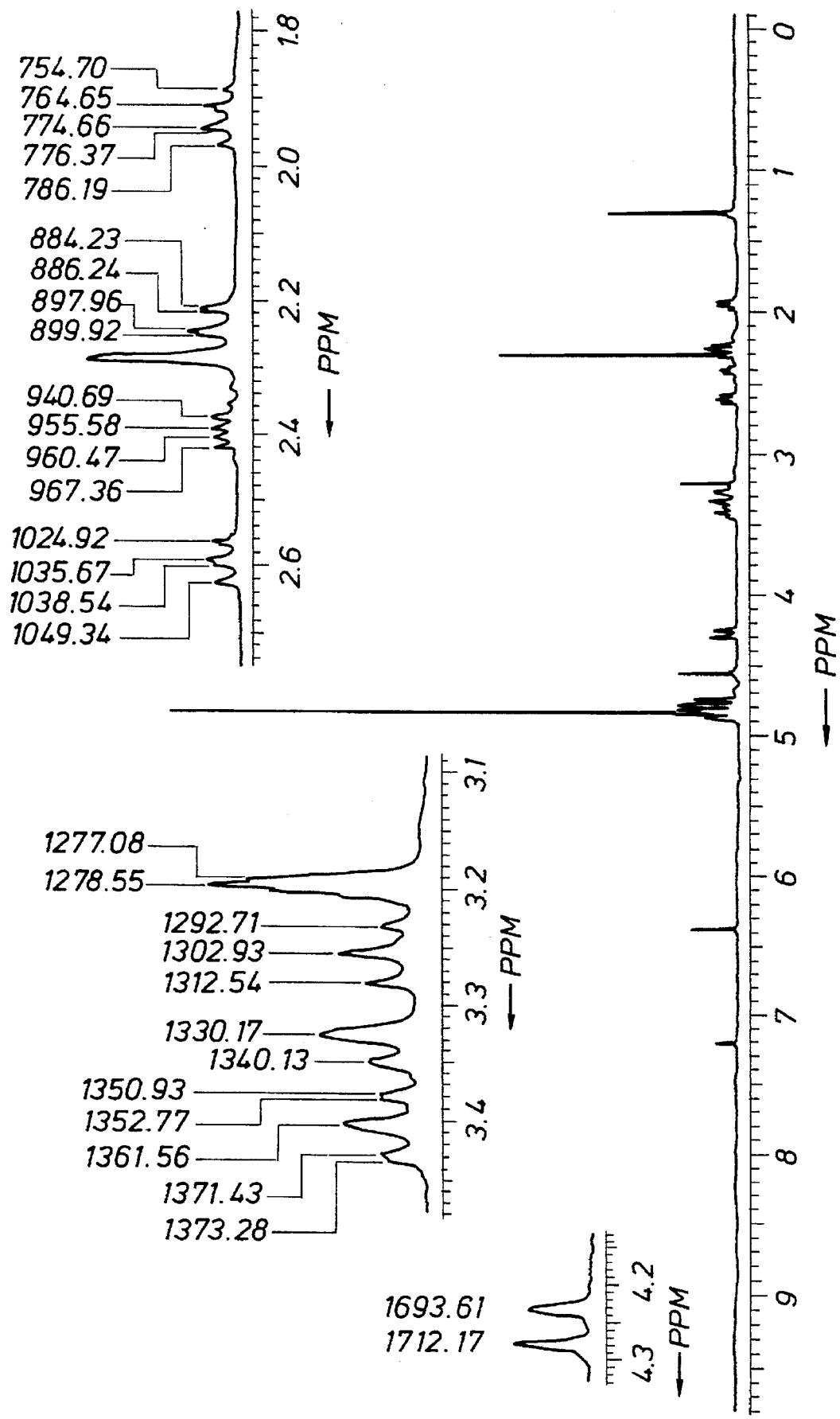

Notably absent in both the $^1$H (FIG. 4) and $^{13}$C NMR spectra were the signature resonances of a terminal methylene, commonly occurring in conjugation with the lactone carbonyl of sesquiterpene lactones, with the appearance of a methyl doublet ($^1$H: δ 1.291,d, J=6.9 Hz, H13; $^{13}$C: δ 15.8). FIG. 4 shows the $^1$H NMR spectra of the active agent. FIG. 4A represents $^1$H NMR spectra in $CD_3OD$; 4B represents $^1$H NMR spectra in $CD_3OD$ plus 3 drops of $C_6D_6$. Insets above 4B are expanded multiplets with frequencies for coupling constant determinations. The sesquiterpene structure was further supported by the presence of a methyl group attached to a vinyl carbon ($^1$H: δ 2.334, br s, 3H: $^{13}$C: δ 21.8) as well as a vinyl hydroxymethyl group ($^1$H: δ 4.305, dd, J=18.7, 1.4 Hz, H15a, and 4.760, dd, J=18.7, 1.9 Hz, H15b; $^{13}$C: δ 63.1), thereby accounting for the three parent methyl groups commonly occurring in sesquiterpenes. The molecular formula as calculated by High Resolution Mass Spectrometry (HRMS) (CI, ammonia, 150 eV: m/z 279.1240, [M+1]$^+$, calculated for $C_{15}H_{17}O_5$ 279.1232) was also in agreement with a sesquiterpene lactone.

The presence of two hydroxyl groups was suggested by the $^1$H and $^{13}$C data in consideration of the molecular formula restrictions. Thus, of the five oxygens required from the HRMS analysis of the molecular ion, three were accounted by the ketone and lactone functionalities. In addition to the hydroxymethyl group, $^{13}$C and $^1$H chemical shifts indicated two other oxygenated sp$^3$hybridized carbons, both methines ($^1$H: δ 3.6, overlapped 2H, resolved to δ 3.257 upon addition of 3 drops benzene-d$_6$, dd, J=10.1, 10.0 Hz, H6; $^{13}$C: δ 82.4; and $^1$H: δ 3.568,ddd, J=10.5,9.9, 1.9, Hz, H8, shifts to δ 3.405 upon addition of 3 drops benzene-d$_6$, ddd, J=10.5, 9.9, 1.9 Hz; $^{13}$C: δ 70.0), the former of which was routinely assigned to the acylated carbinol carbon of the lactone functionality (C/H-9) on the basis of its lower field carbon chemical shift. The latter resonance was therefore considered to belong to a secondary alcohol.

The UV spectrum ($\lambda_{max}$ 225 nm, MeOH) and the one of the two carbonyl stretching bands in the infrared spectrum ($CHCl_3$: 1685 cm$^{-1}$) were very reminiscent of the substituted 5-methyleno-2-cyclopentenone chromophore also present in lactucin as noted in Phytochemistry 1982 21,1163. This subunit also accounted for the four noncarbonyl sp$^2$hybridized carbons present in the $^{13}$C NMR spectrum as well as the coupling pattern observed in the homonuclear $^1$H COSY (correlated spectroscopy) spectrum (FIG. 5).

Figure 5:
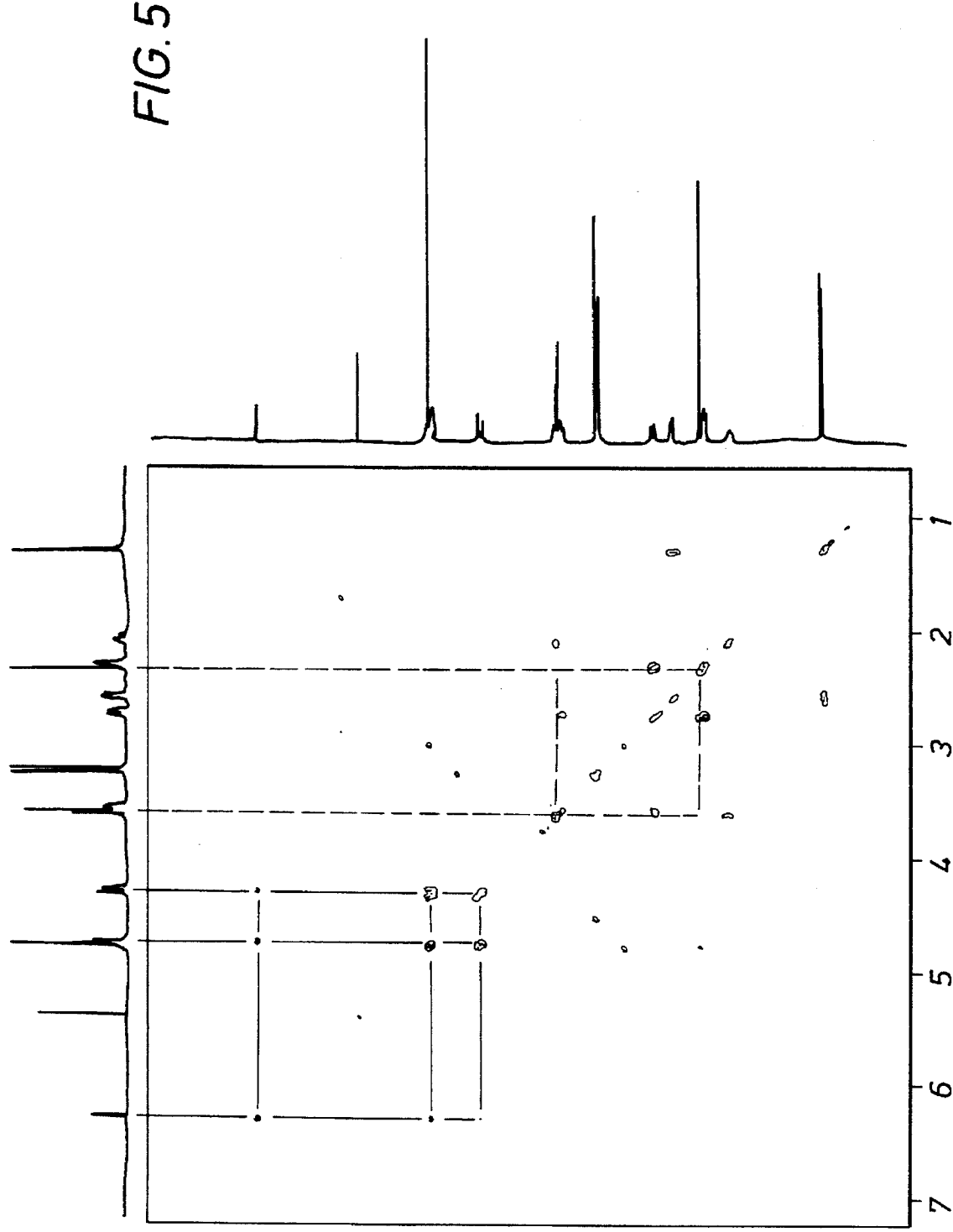
FIG. 5 depicts homonuclear $^1$H COSY spectra of the purified active agent in $CD_3OD$.
Figure 6:
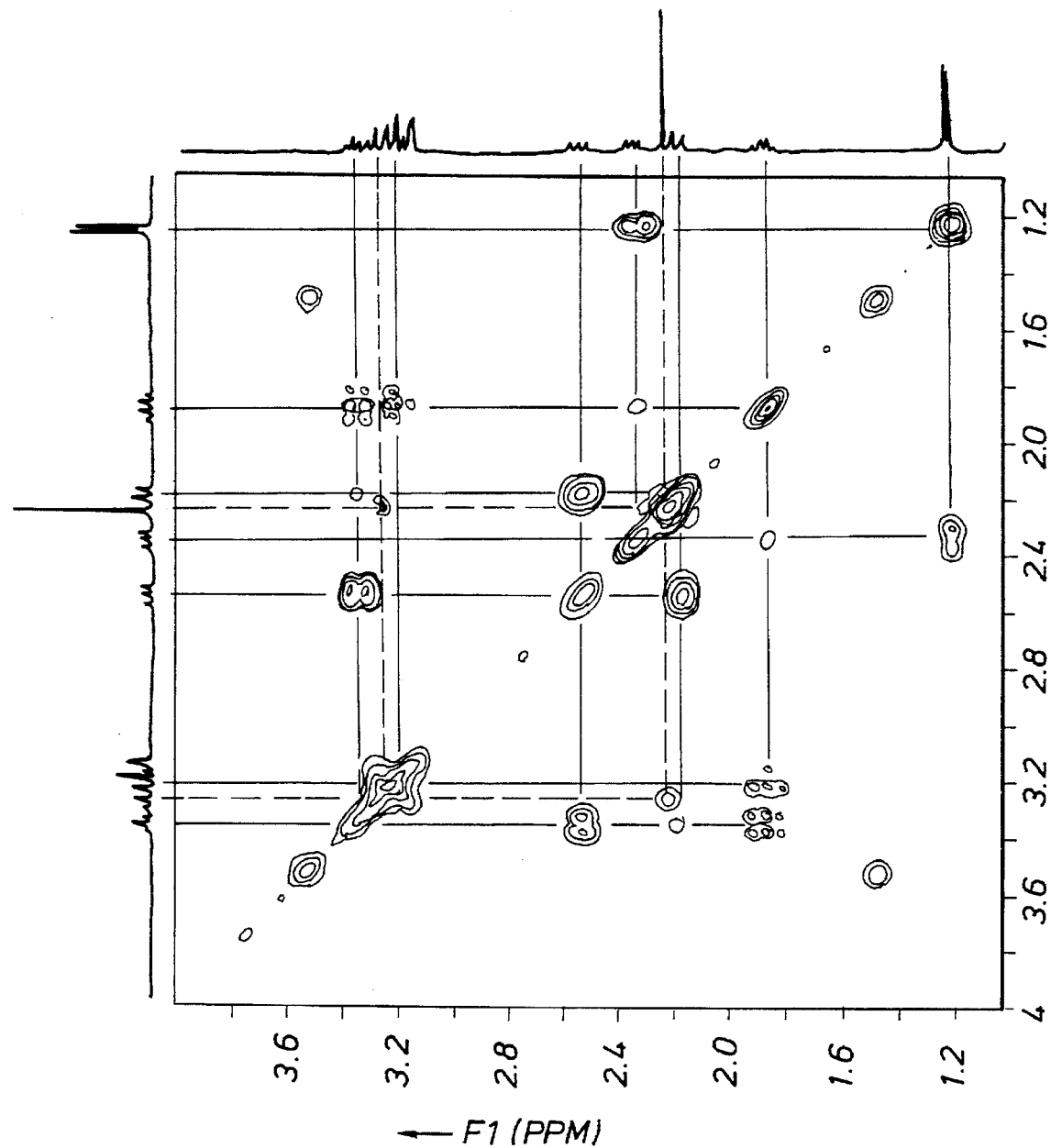
FIG. 6 depicts COSY spectra of the purified active agent in $CD_3OD$ after addition of three drops of benzene-$d_6$.

FIG. 5 shows the homonuclear $^1$H COSY spectrum of the active agent. Allylic couplings between H3 and both H15 hydroxymethyl protons (solid lines) as well as homoallylic coupling between H14 and H5 (dashed lines) are indicated. Thus, a vinyl proton in the $^1$H NMR spectrum appeared as broad singlet, but which could be resolved into a narrowly coupled multiplet, suggesting allylic coupling (δ 6.310, dd, J=1.9, 1.4 Hz, H3). The COSY spectrum indicated weak coupling between this vinyl proton and both methylene protons of the vinylic hydroxymethyl group. This allylic coupling therefore located the hydroxymethyl group at the β-position of the trisubstituted double bond, and not on the tetrasubstituted double bond. (The vinyl proton must be located on the α-position since a heteronuclear COSY spectrum showed this proton to be bonded to a carbon with a resonance of δ 133.1). The remaining methine of the chromophore was initially located in the δ 3.6 overlapped region by weak coupling with the vinylic methyl group (H14) observed in the COSY spectrum. This homoallylic coupling was more cleanly observed upon addition of three drops of benzene-d$_6$ (FIG. 6), which resolved all the proton resonances. FIG. 6 shows the COSY spectrum after addition of benzene-d$_6$. Vicinal couplings mapping the H5 through H9 spin system including H11 and H13 are shown in solid lines; homoallylic coupling between H14 and H5 is shown in dashed lines. In this solvent, coupling between the vinyl methyl (shifted to δ 2.284 by the benzene-d$_6$) with a broad doublet (δ 3.338,br d, J=10.0 Hz, H5; $^{13}$C δ 50.0) enabled expansion of the chromophore to Substructure I.

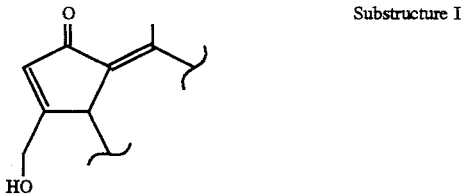

Substructure I

Substructure I and the lactone functionalities accounted for six of the seven units of unsaturation required by the molecular formula and indicated that the active agent was a guaianolide sesquiterpene, the last unit of unsaturation being the central seven-membered ring. The COSY spectrum completely mapped the proton coupling network which extended around the seven membered ring and through the lactone (FIG. 6). Thus, the resolved (upon addition of three drops of benzene-d$_6$) chromophoric methine (H5) coupled with the acylated carbinol proton of the lactone functionality (H-6: δ 3.6 overlapped with H5 in methanol-d$_4$, resolved upon addition of benzened-d$_6$, δ 3.257,dd, J=10.1, 10.0 Hz; $^{13}$C: δ 82.4) with a coupling constant which required a trans orientation between H5 and H6 (J=10.0 Hz); H6 in turn coupled with one other methine (δ 2.085, ddd, J=11.8, 10.1, 9.9 Hz, H7, shifts to δ 1.927 upon addition of benzene-d$_6$; $^{13}$C: δ 62.3). This methine coupled with two other methines in addition to coupling with H6 with coupling constants also indicative of trans couplings (H8: δ 3.568, partially overlapped ddd, resolved upon addition of benzene-d$_6$: δ 3.405, ddd, J=10.5, 9.9, 1.9 Hz; $^{13}$C: δ 70.0; and δ 2.570, dq, J=11.8, 6.9 Hz, H11; $^{13}$C: δ 42.5). The latter methine (H11), with a chemical shift suggestive of a proton α to a carbonyl group, coupled with the methyl doublet, completing the lactone ring substructure. The former methine resonance (H8); which is the carbinol proton of the secondary alcohol functionality, coupled with the two protons of an allylic methylene (δ 2.301,dd, J=13.7,2.0 Hz, H9 β; 2.730,dd, J=10.7, 13.7 Hz, H9 α; $^{13}$C: δ 49.7); the allylic nature of this methylene group was subsequently confirmed by selective Insensitive Nuclei Enhanced by Polarization Transfer (INEPT) studies. The distinct couplings between the C9 methylene protons and H8 indicated the predominance of a single conformation with H8 oriented in axial fashion.

Figure 7:
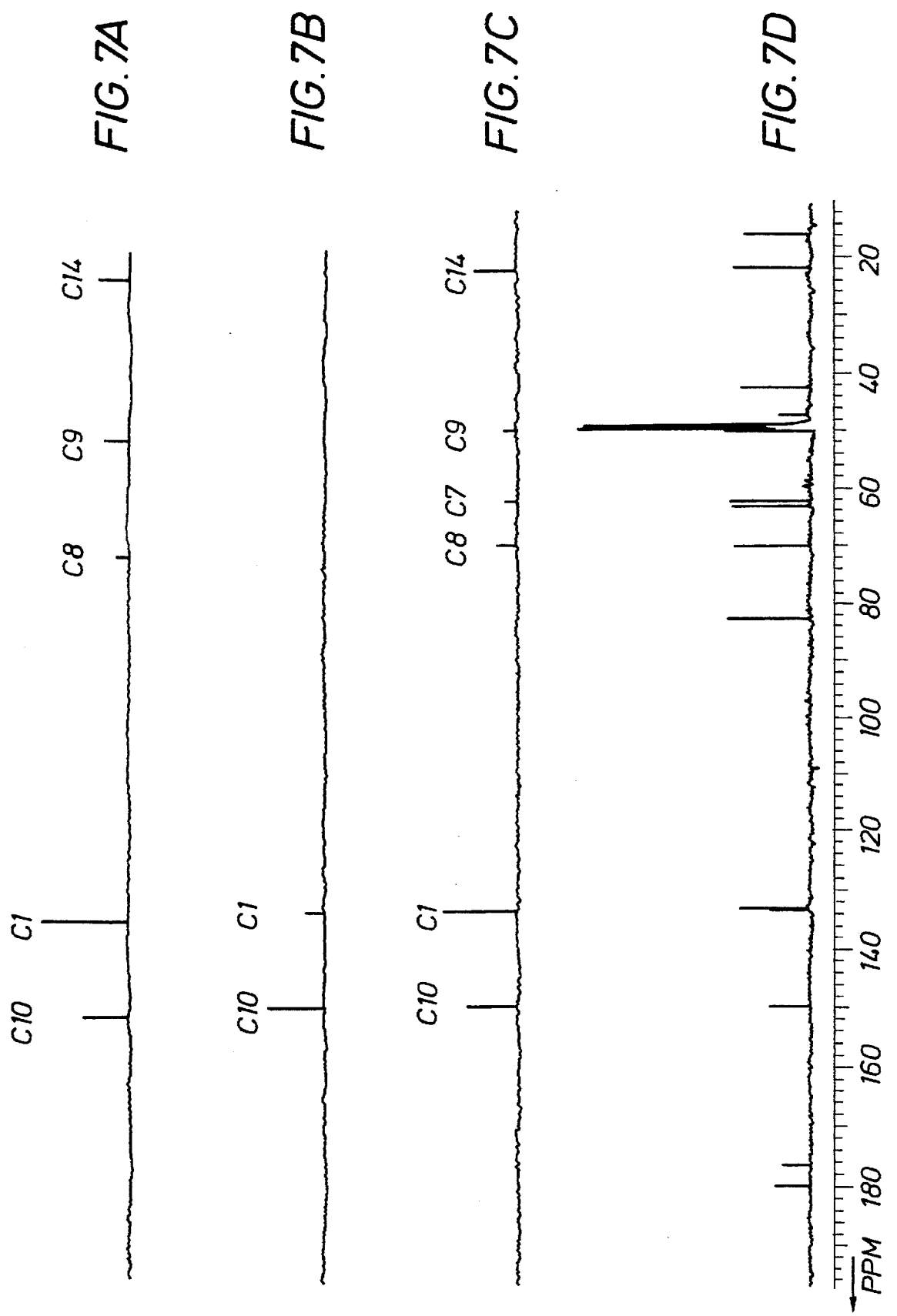
FIG. 7 depicts selective INEPT experiments in $CD_3OD$.

The mapping of the proton coupled spin system from the cross-conjugated substituted α-methylenocyclopentenone chromophore through the lactone ring as well as through the C9 methylene protons using the COSY spectrum supported the guaianolide structure. Closing of the central seven membered ring at C9–C10 was confirmed by heteronuclear $^1$H/$^{13}$C couplings observed through several selective INEPT experiments. FIG. 7 shows selective INEPT experiments in CD$_3$OD. FIG. 7(A) shows saturation of H9 β (δ 2.301); (B) shows saturation of H9 α (δ 2.730); (C) reveals saturation of H14 (δ 2.334); (D) represents the broad-band decoupled 13C spectrum. Thus, saturation of H9 α methylene proton in methanol-d$_4$ resulted in an enhancement of only the C1 and C10 vinyl resonances (δ 133.6 and 149.9, respectively, routinely distinguished by their chemical shifts), but saturation of H9 β also enhanced the resonance of C14, as well as those of C8 and C9. Heteronuclear polarization transfer in the reciprocal direction (from the chromophore to the seven membered ring) was observed upon saturation of the H14 methyl singlet, which results in an enhancement of the C9 resonance. (Enhancement of the C7 and C8 resonances in this latter spectrum, FIG. 7C, are a consequence of the partial overlap of the H14 and H9 β resonances resulting in partial saturation of this latter signal and hence polarization transfers to C7 and C8).

Figure 8:
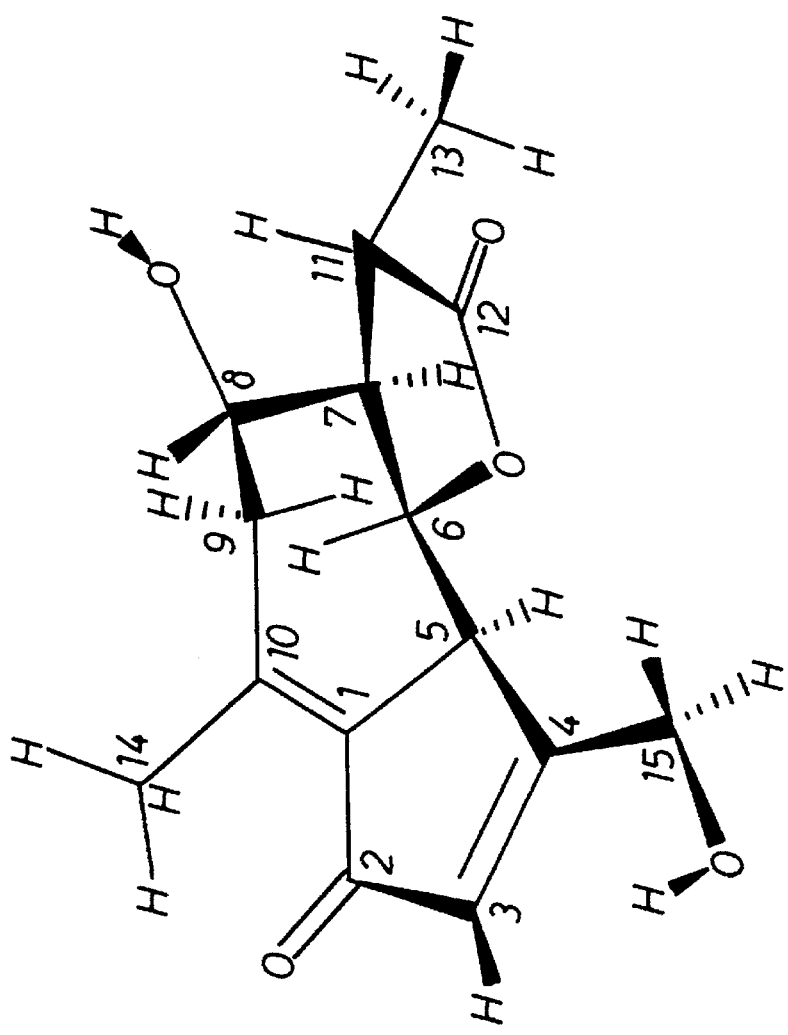
FIG. 8 is the solution conformation of the purified active agent of the present invention from MM2 calculation.

With the carboskeleton of the active agent resolved, the assignment of the relative stereochemistry, as well as completion of the assignment of the nonprotonated carbons remained. The series of vicinal coupling constants linking H5 through H8 suggested an all trans diaxial arrangement of these protons. Furthermore, $^3J_{7,11}$ of 11.8 Hz also suggested a trans relationship between these protons. This relative stereochemistry was confirmed by 2-dimensional Nuclear Overhauser Effect (2D-NOE) studies in methanol-d$_4$ with 3 drops of benzene-d$_6$. Mutual NOE's between H6, H8 and H11 indicated that these three protoms were on the same face of the molecule. In addition, mutual NOE's between H7, H$_5$, H9 α (the downfield proton of the C9 methylene pair with trans-diaxial coupling with H8), as well as between H7 and H13 methyl protons defined the α-face orientation of these protons. The conformation determined from these NOE's as well as the vicinal coupling constants was in agreement with that predicted by Molecular Modeling 2 (MM2) calculations (FIG. 8).

The relative stereochemistry required by these NOE's confirmed that predicted from the coupling constants and indicated that the active agent was 11β,13-dihydrolactucin, originally isolated from *Launaea mucronata* (*Phytochemistry* 1982, 21, 1163) and more recently also reported from the roots of *Cichorium endivia* (*Chem. Pharm. Bull.* 1988, 36, 2423). In this latter report, the 15-glucoside of 11β,13-dihydrolactucin was also reported from the roots of *C. intybus*, but the parent aglycone, 11β,13-dihydrolactucin, was not reported.

Figure 9:
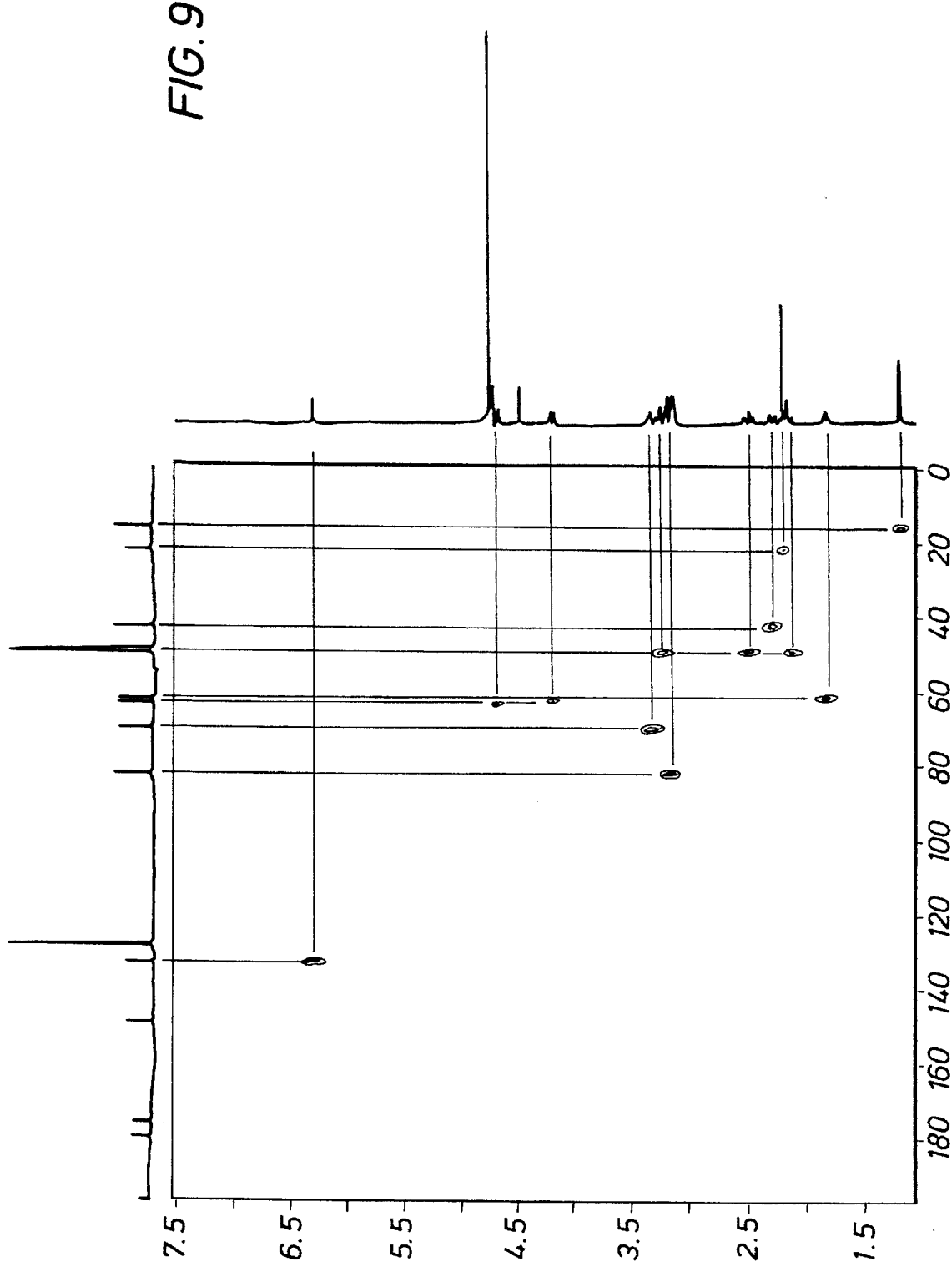
FIG. 9 depicts the heteronuclear COSY spectra of the purified active agent in $CD_3OD$ plus 3 drops of benzene-$d_6$.

With the structure confirmed and the proton assignments completed, the $^{13}$C assignments of the protonated carbons was routine from the heteronuclear COSY spectrum (FIG. 9). The $^{13}$C assignments of the nonprotonated carbons were completed on the basis of their chemical shifts, and by selective INEPT studies. As previously mentioned, C1 and C10 were enhanced by polarization transfers from saturation of both H9 proton resonances, and further distinguished on the basis of their chemical shifts, with the carbon β to the carbonyl being the farther downfield. (The selective INEPT experiment enabled distinction of C4 vs C10); C3 and C4, as well as the ketonic and lactonic carbonyls were similarly distinguished on the basis of their relative chemical shifts (Table 17).

TABLE 17

$^1$H and $^{13}$C NMR Chemical Shifts Of Substructure I

| H/C | $^1$H:CD$_3$OD | $^1$H:CD$_3$OD + C$_6$D$_6$ (3 drops) | $^{13}$C:CD$_3$OD* |
|---|---|---|---|
| 1 | | | 133.6(s) |
| 2 | | | 197.4(s) |
| 3 | 6.310 (dd, J=1.9, 1.4 Hz) | 6.359(bs) | 133.1(d) |
| 4 | | | 176.5(s) |
| 5 | 3.6 (overlapped) | 3.338(bd, J=10.0Hz) | 50.0(d) |
| 6 | 3.6 (overlapped) | 3.257(ddd, J=10.1, 10.0, Hz) | 82.4(d) |
| 7 | 2.085(ddd, J=11.8, 10.1, 9.9 Hz) | 1.927 (ddd, J=11.8, 10.1, 9.9 Hz) | 62.3(d) |
| 8 | 3.568(ddd, J=10.7, 9.9, 2.0 Hz | 3.405 (ddd, J=10.5, 9.9, 1.9 Hz) | 70.0(d) |
| 9 | α: 2.730 (dd, J=13.7, 10.7 Hz) | α 2.594 (dd, J=13.7, 10.5 Hz) | 49.7(t) |
|   | β: 2.301 (dd, J=13.7, 2.0 Hz) | β: 2.235 (dd, J=13.7, 1.9 Hz) | |
| 10 | | | 149.9(s) |
| 11 | 2.570(dq, J=11.8, 6.9 Hz) | 2.395 (dq, J=11.8, 6.9 Hz) | 42.5(d) |
| 12 | | | 180.0 |
| 13 | 1.291 (d, J=6.9 Hz) | 1.283 (d, J=6.9 Hz) | 15.8 |
| 14 | 2.334(bs) | 2.284(bs) | 21.8 |
| 15 | 4.760 (dd, J=18.7, 1.9 Hz) | 4.748 (bd, J=18.5 Hz) | 63.1(t) |
|    | 4.305 (dd, J=18.7, 1.4 Hz) | 4.248 (bd, J=18.5 Hz) | |

The foregoing demonstrates that the preferred purified active agent of the present invention is 11β,13-dihydrolactucin, the official name of which is 3,6-dimethyl-4-hydroxy-9-hydroxymethyl-3,3a,4,5,9a,9b hexahydroazuleno[4,5-b]furan-2,7-dione.

Many other variations and modifications may be made in the methods herein described, by those having experience in this art, without departing from the concept of the present invention. Accordingly, it should be clearly understood that the methods described in the foregoing description are illustrative only, and not intended as a limitation on the scope of the invention.

What is claimed is:

1. A method for treating a neoplastic disorder in an animal comprising, administering an effective amount of an agent having the structure:

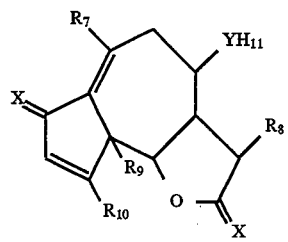

where X is O, S, or nitrogen as imines (=NR') or hydrazones (NR'NR'$_2$), where Y is either O or S, and wherein each or any of R$_7$, R$_8$, R$_9$, and R$_{10}$ is:

(1) a substituent selected from group consisting of hydrogen (H—), halogen (for example, chloro, fluoro, or bromo), hydroxyl (—OH), alkoxyl (—OR'),

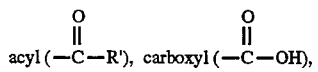

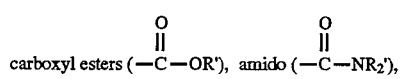

amino (—NR'$_2$), nitro (—NO$_2$), nitroso (—NO), azo (—N=N—), diazonium (—N$_2^\oplus$), azido (—N$_3$), hydrazino (—NR'—NR'$_2$), cyano (NC—), isocyano (CN—), cyanato (NCO—), isocyanato (OCN—), thioether (—SR'), thiol (—SH),

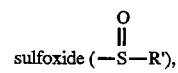

sulfone (—S(O)$_2$R'), sulfonic acid (HO$_3$S—), sulfonyl esters (R'O$_3$S—), sulfinic acid (HO$_2$S—), sulfinyl esters, (R'O$_2$S—), sulfenic acid (HOS—), sulfenyl ester (R'OS—),

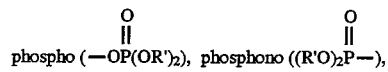

or phosphine (—PR'$_2$), where R' is an alkyl, alkenyl or alkynyl of 1–5 carbons; or (2) an unsaturated or saturated aliphatic, alicyclic or aromatic hydrocarbon radical having from 1–5 carbon atoms which can be substituted with one or more of the substituents of (1) above to an animal having a neoplastic disorder selected from the group consisting of lymphomas, adenocarcinomas, mastocytomas, myelomas, pulmonary tumors, sarcomas and macrophage tumors.

2. A method according to claim 1 in which X is O, Y is O, R$_7$ is methyl, R$_8$ and R$_9$ is hydrogen, and R$_{10}$ is —CH$_2$OH.

3. A method according to claim 1 wherein the agent is a sesquiterpene lactone.

4. A method according to claim 3 wherein the sesquiterpene lactone is a guaianolide sesquiterpene lactone.

5. A method according to claim 4 wherein the guaianolide sesquiterpene lactone is a lactucin.

6. A method according to claim 5 wherein the lactucin is 11β,13-dihydrolactucin.

* * * * *